United States Patent
Gualandi et al.

(10) Patent No.: US 10,098,976 B2
(45) Date of Patent: Oct. 16, 2018

(54) ANTIBODIES FOR TREATMENT AND DIAGNOSIS

(71) Applicant: Philogen S.P.A., Siena (IT)

(72) Inventors: Laura Gualandi, Zürich (CH); Sarah Wulhfard, Neuenhof (CH); Catherine Hutchinson, Brugg (CH); Mattia Matasci, Zürich (CH)

(73) Assignee: Philogen S.P.A., Siena (IT)

( * ) Notice: Subject to any disclaimer, the term of this patent is extended or adjusted under 35 U.S.C. 154(b) by 81 days.

(21) Appl. No.: 15/329,223

(22) PCT Filed: Jul. 28, 2015

(86) PCT No.: PCT/EP2015/067309
§ 371 (c)(1),
(2) Date: Jan. 25, 2017

(87) PCT Pub. No.: WO2016/016265
PCT Pub. Date: Feb. 4, 2016

(65) Prior Publication Data
US 2018/0193496 A1    Jul. 12, 2018

(30) Foreign Application Priority Data
Jul. 28, 2014 (GB) .................. 1413357.3

(51) Int. Cl.
| | | |
|---|---|---|
| *A61K 39/395* | (2006.01) | |
| *A61K 51/10* | (2006.01) | |
| *G01N 33/564* | (2006.01) | |
| *G01N 33/574* | (2006.01) | |
| *C07K 16/18* | (2006.01) | |
| *A61K 47/68* | (2017.01) | |
| *A61P 35/00* | (2006.01) | |
| *C07K 16/40* | (2006.01) | |
| *A61K 39/00* | (2006.01) | |

(52) U.S. Cl.
CPC ...... *A61K 51/1018* (2013.01); *A61K 39/3955* (2013.01); *A61K 47/6803* (2017.08); *A61P 35/00* (2018.01); *C07K 16/18* (2013.01); *C07K 16/40* (2013.01); *G01N 33/564* (2013.01); *G01N 33/574* (2013.01); *A61K 2039/505* (2013.01)

(58) Field of Classification Search
None
See application file for complete search history.

(56) References Cited

FOREIGN PATENT DOCUMENTS

WO    WO 03/019136    3/2003

OTHER PUBLICATIONS

Bramhall et al., "Expression of collagenase (MMP2), stromelysin (MMP3) and tissue inhibitor of the metalloproteinases (TIMP1) in pacreatic and ampullary disease," *British Journal of Cancer*, vol. 73, No. 8, pp. 972-978, 1996.
Brellier et al., "Tenascin-W is a better cancer biomarker than tenascin-C for most human solid tumors," *BMC Clinical Pathology*, 12:14, 2012 (10 pages).
Elices et al., "Expression and Functional Significance of Alternatively Spliced CS1 Fibronectin in Rheumatoid Arthritis Microvasculature," *Journal of Clinical Investigation*, vol. 93, No. 1, pp. 405-416, 1994.
Garcia-Pardo et al., "Two novel monoclonal antibodies to fibronectin that recognize the hep II and CS-1 regions respectively: Their differential effect on lymphocyte adhesion," *Biochemical and Biophysical Research Communications*, vol. 186, No. 1, pp. 135-142, 1992.
Kamarajan et al., "The CS1 segment of fibronectin is involved in human OSCC pathogenesis by mediating OSCC cell spreading, migration, and invasion," *BMC Cancer*, 10:330, 2010 (8 pages).
Santas et al., "Alternative Splicing of the IIICS Domain in Fibronectin Governs the Role of the Heparin II Domain in Fibrillogenesis and Cell Spreading," *Journal of Biological Chemistry*, vol. 277, No. 16, pp. 13650-13658, 2002.
Tai et al., "Periostin induction in tumor cell line explants and inhibition of in vitro cell growth by anti-periostin antibodies," *Carcinogenesis*, vol. 26, No. 5, pp. 908-915, 2005.
Warawdekar et al., "Elevated levels and fragmented nature of cellular fibronectin in the plasma of gastrointestinal and head and neck cancer patients," *Clinica Chimica Acta*, vol. 372, Nos. 1-2, pp. 83-93, 2006.
Zhu et al., "Neutralizing monoclonal antibody to periostin inhibits ovarian tumor growth and metastasis," *Molecular Cancer Therapeutics*, vol. 10, No. 8, pp. 1500-1508, 2011.

*Primary Examiner* — Laura B Goddard
*Assistant Examiner* — Meera Natarajan
(74) *Attorney, Agent, or Firm* — Klarquist Sparkman, LLP

(57) ABSTRACT

The invention relates to the diagnosis and treatment of diseases, including cancer and inflammatory disorders. The invention provides, and involves the use of, antibodies that bind: i) the IIICS isoform of fibronectin, ii) matrix-metalloproteinase 3 (MMP3), iii) periostin, or iv) tenascin-W.

20 Claims, 7 Drawing Sheets

Specification includes a Sequence Listing.

ANTIBODIES FOR TREATMENT AND DIAGNOSIS

CROSS REFERENCE TO RELATED APPLICATIONS

This is the § 371 U.S. National Stage of International Application No. PCT/EP2015/067309, filed Jul. 28, 2015, which was published in English under PCT Article 21(2), which in turn claims the benefit of GB Application No. 1413357.3, filed Jul. 28, 2014, which is incorporated by reference herein in its entirety.

FIELD OF THE INVENTION

The present invention relates to the diagnosis and treatment of diseases, including cancer and inflammatory disorders. The invention provides, and involves the use of, antibodies that bind: i) the IIICS isoform of fibronectin, ii) matrix-metalloproteinase 3 (MMP3), iii) periostin, or iv) tenascin-W.

BACKGROUND TO THE INVENTION

Most conventional pharmaceuticals currently in use for the treatment of serious disorders such as cancer and inflammatory diseases do not selectively accumulate at the site of disease [Bosslet et al., 58, 1195-1201 Cancer Res. (1998)]. For example, intravenously administered drugs distribute evenly within the different organs and tissues of the body, rather than selectively accumulating at the site of disease.

One approach to circumvent the disadvantages of conventional pharmacological therapies involves the preferential delivery of a bioactive agent to the site of disease by means of a binding molecule specific for a pathology-associated marker [Neri & Bicknell (2005) Nature Rev. Cancer, 4, 436-446]. The selective targeting of the drug to the diseased tissue will ultimately result in an increased local concentration at its site of action, sparing normal organs from the unwanted effects of the bioactive agent used to confer a pharmacological benefit (e.g., a growth factor, an enzyme, a hormone, an anti-inflammatory drug, a cytotoxic drug, a cytokine, a radionuclide, a photosensitizer). In most cases, this will lead to an improved therapeutic index of the delivered pharmaceutical, i.e. a higher efficacy with minimized side effects. Indeed, the favourable toxicity profile of site-specific therapeutics may open new avenues in the therapy of angiogenesis-related diseases, allowing the systemic administration of highly potent and promising agents, which are currently either given at suboptimal doses or whose clinical application has to date been impeded by unacceptable side-effects when applied in an unmodified form.

Ligand-based pharmacodelivery strategies fundamentally rely on the identification of good-quality markers of pathology, allowing a clear-cut discrimination between diseased tissues and healthy organs. Monoclonal antibodies and their fragments represent the preferred agents for pharmacodelivery applications [Rybak et al. 2, 22-40 Chem. Med. Chem (2007); Shrama et al., 5, 147-159 Nat. Rev. Drug Discovery (2006)], but globular protein mutants [Binz and Plückthun, 23, 1257-1268 Nature Biotechnology (2005)], peptides [Sergeeva et al., 58, 1622-1654, Adv. Drug. Deliv. Rev. (2006)] and even small organic ligands [Low et al., 41, 120-129, Acc. Chem. Res. (2008)] are also increasingly being used.

Antibody-based targeted delivery of bioactive agents to sites of angiogenesis as a therapeutic strategy for cancer treatment has been described. In the case of inflammatory disorders, antibody-based targeted delivery is much less well studied. The applicant has previously demonstrated that the ED-A domain of fibronectin, and the ED-B domain of fibronectin, two marker of angiogenesis, are expressed in the arthritic paws in the collagen-induced mouse model of rheumatoid arthritis. Using both radioactive and fluorescent techniques, the human monoclonal antibody F8, specific to ED-A, and the human monoclonal antibody L19, specific to ED-B, were found to selectively localize at sites of inflammation in vivo, following intravenous administration. When such antibodies were fused to the anti-inflammatory cytokine interleukin-10 the conjugate strong therapeutic activity was also shown (PCT/EP2007/004044, PCT/EP2008/009070). Nevertheless there remains a need in the art for further antibodies which can be employed in ligand-based pharmacodelivery applications for the treatment and diagnosis of diseases, such as cancer and inflammatory disorders.

IIICS Isoform of Fibronectin

Fibronectins (FN) are multifunctional, high molecular weight glycoprotein constituents of both the extracellular matrix and body fluids. They are involved in many different biological processes such as the establishment and maintenance of normal cell morphology, cell migration, haemostasis and thrombosis, wound healing and oncogenic transformation [Alitalo et al., (1982) Adv Cancer Res, 37 111-158; Yamada, (1983) Curr Opin Cell Biol, 1, 956-963; Hynes, (1985) Annu Rev Cell Biol, 1, 67-90; Ruoslahti et al., (1988) Annu Rev Biochem, 57, 375-413; Owens et al., (1986) Oxf Sury Eukaryot Gene, 3, 141-160]. Structural diversity in FNs is brought about by alternative splicing of three regions (ED-A, ED-B and IIICS) of the primary FN transcript (Hynes, R., (1985) Annu Rev Cell Biol, 1, 67-90; Zardi et al., (1987) EMBO J, 6, 2337-2342) to generate at least 20 different isoforms, some of which are differentially expressed in tumour and normal tissue. For example, five different splice isoforms of the human IIICS isoform of fibronectin have been described. As well as being regulated in a tissue- and developmentally specific manner, it is known that the splicing pattern of FN-pre-mRNA is deregulated in transformed cells and in malignancies (Castellani et al., (1986) J Cell Biol, 103, 1671-1677; Borsi et al., (1987) J Cell Biol, 104, 595-600; Vartio et al., (1987) J Cell Sci 88, 419-430, Zardi et al., (1987) EMBO J, 6, 2337-2342; Barone et al., (1989) EMBO J, 8, 1079-1085; Carnemolla et al., (1989) FEBS Letter 215, 269-273; Oyama et al., (1989) Biochemistry, 28, 1428-1433; Borsi et al., (1992) Exp Cell Res 199, 98-105). The FN isoforms containing the ED-A, ED-B and IIICS sequences are expressed to a greater extent in transformed and malignant tumour cells than in normal cells.

Much of the information relating to the expression of the IIICS isoform of fibronectin in healthy and diseased tissues derives either from mRNA studies or from studies with monoclonal antibodies (antibodies FDC-6 and X18A4). These antibodies were generated by hybridoma technology following immunization with fibronectin and immunosuppression with cyclophosphamide. Antibody FDC-6 binds to a specific O-linked N-acetygalactosaminylated hexapeptide epitope within the fibronectin type III connecting segment (IIICS) [Matsuura et al., (1985) PNAS, 82, 6517-6521; Matsuura et al., (1988) J Biol Chem, 263, 3314-3322]. However, since the antibody requires both the peptide backbone and the carbohydrate moiety to recognize the epitope, it is not suitable for targeting application especially when cross-reactivity between species is needed. Antibody X18A4 recognizes a different IIICS region than FDC-6, but the binding epitope has never been fully characterized [Feinberg R. et al., (1995) Am J Obstet Gynecol, 172, 1526-1536]: the main application for antibody X18A4 is related to the detection of oncofetal fibronectin in the cervix of pregnant women to predict preterm labour. There is evidence that IIICS expression is modulated in rheumatoid arthritis and osteoarthritis: in particular, it seems that the isoform 89V (CS1) is up-regulated in inflammation [Kriegsmann J et al., (2004) Rheumatol Int, 24, 25-33; Elices M J et al., (1994) J Clin Invest, 93, 405-416].

Matrix-metalloproteinase 3 (MMP3)

Matrix metalloproteinase 3 (also known as stromelysin 1) is a member of a family of more than 20 zinc-dependent extracellular enzymes with a key role in tissue remodeling [Nagase and Woessner, (1999) J Biol Chem, 274, 21491-21494; Martin and Matrisian, (2007) Cancer Metastasis Rev, 26, 717-724; Vartak and Gemeinhart, (2007) J Drug Target 15(1) 1-20]. Abnormal expression of various MMP proteins has been shown to play a role in a variety of disease types including cancer progression and in inflammatory conditions such as rheumatoid arthritis [Martin and Matrisian, (2007) Cancer Metastasis Rev, 26, 717-724; Brinckerhoff and Matrisian, (2002) Nat Rev Mol Cell Biol, 3, 207-214; Overall and Kleifeld, (2006) Nat Rev Cancer, 6, 227-239]. The catalytic domain of MMP3 is known to be relatively well conserved between mouse, rat and man.

Periostin

Periostin or Osteoblast Specific Factor 2 (OSF-2) was described for the first time in 1999 by the group of A. Kudo as a dimeric protein of 90 kDa secreted by osteoblasts and osteoblast-like cell lines. Periostin is mainly localized in the extracellular matrix of the periosteum and its main function is to act as a cell adhesion molecule for preosteoblasts and to induce osteoblast attachment and spreading [Horiuchi K et al., (1999) J Bone Miner Res, 14, 1239-1249].

The periostin N-terminal region contains four fasciclin-like domains (FAS1-4) as well as several glycosylation sites. Six different splice isoforms of periostin have been reported, but only four of them have been sequenced and annotated: these splice isoforms are characterized by the presence or absence of casette exons 17 to 21 at the C-terminus of the protein [Castronovo et al., (2006) Mol Cell Proteomics, 5, 2083-2091; Litvin et al., (2004) J Cell Biochem, 95, 1044-1061; Kim et al., (2008) Int J Oncol, 32, 161-169].

Tai and colleagues produced a monoclonal anti-periostin antibody by hybridoma technology and detected, by Western blotting, expression of the human periostin protein in the adrenal glands, lung, thyroid, uterus, vagina, ovary, testis, prostate, and in the gastrointestinal tract, with a preferential expression in the stomach and colorectum, while lower levels were noted in the small intestine and esophagus (Tai et al., Carcinogenesis, 26, 908-15, 2005). There have been observations of periostin being associated with a number of disorders. For instance, Morra and Moch [Virchows Archives., (2011) 459, 465-475] described the role of periostin in tumor microenviroment and tumor development. The N-terminal domain, with the FAS domains, bind to integrins and activates the Akt/PKB and the FAK-mediated signaling pathways, thus leading to tumor invasion and metastasis. The C-terminus of the protein binds to ECM molecules and influences the organization of the ECM. It is not yet clear if the different splice isoforms play different roles in ECM modification in tumor invasion.

In an in vivo chemical proteomic analysis, based on the terminal perfusion of three mouse models of liver metastases, periostin was one of the most abundant accessible antigens identified [Borgia et al., (2010) Cancer Res, 70, 309-318]. Immunofluorescence analysis confirmed the proteomic findings, indicating that periostin can be expressed in the neovasculature of tissues undergoing extensive remodeling.

Tenascin-W

Tenascin-W is the most recently discovered member of the tenascin gene family. Human tenascin-W is composed of a modular structure shared with all other tenascins (i.e. tenascin-C, -R, and -X respectively), which includes: N-terminal heptad repeats, 3.5 EGF-like repeats, 9 FN III domains and a C-terminal fibrinogen-related domain. In contrast to other tenascin family members, the existence of tenascin-W splice isoforms has not been reported to date [Chiquet-Ehrismann et al., (2011) Cold Spring Harb Perspect Biol. 3 (5), doi: 10.1101/cshperspect.a004960].

During embryonic development, tenascin-W is predominantly expressed in the extracellular matrix of periosteal bone, and to a lesser extent in smooth muscle, tendons and ligaments [Weber et al., (1998) J Neurobiol, 35, 1-16; Scherberich et al., (2004) J Cell Sci, 117, 571-581; Meloty-Kapella et al., (2006) Dev Dyn, 235, 1532-1542]. In healthy adults, the expression of tenascin-W is strongly reduced and restricted to the kidney, cardiac valves, corneal limbus and periosteum [Scherberich et al., (2004) J Cell Sci, 117, 571-581]. Tenascin-W expression has been detected in the perichondrium/periosteum during endochondral ossification and bone fracture repair [Kimura et al., (2007) Biochem Biophys Res Commum, 356, 935-941], suggesting its association with osteogenesis [Martina et al., (2010) Int J Biochem Cell Biol, 42, 1412-1415].

Tenascin-W is a tumour-associated antigen; its expression partly overlaps with tenascin-C in various cancers. To date tenascin-W expression has been detected in the stroma of breast [Degen et al., (2007) Cancer Res, 67, 9169-9179], and colorectal cancer [Degen et al., (2008) Int J Cancer, 122, 2454-2461], gliomas [Martina et al., (2010) FASEB J, 24, 778-787], melanomas, as well as pancreatic, kidney, and lung carcinomas [Brellier et al., (2012) BMC Clin Pathol, 4, 12-14]. Tenascin-W was not detectable in the corresponding healthy tissues. Interestingly, in most tumor types, tenascin-W was detected in the perivascular region of newly formed blood vessels [Brellier et al., (2012) BMC Clin Pathol, 4, 12-14, Martina et al., (2010) FASEB J, 24, 778-787].

The amino acid sequence of tenascin-W is highly conserved, between human, mouse and rat. However two major differences are present. Firstly, the three tenascin-W orthologues differ in the number of FNIII domains, with the mouse and rat variants containing 3 additional FNIII domains. Secondly, the mouse and rat tenascin-W genes contain a putative integrin binding RGD motif located in the second FNIII domain, which is absent in the human orthologue.

SUMMARY OF THE INVENTION

The present invention relates to the provision of novel antibody molecules for use in therapeutic and/or diagnostic applications. In particular, the antibody molecules of the present invention find use in pharmacodelivery applications.

Specifically, the present inventors have isolated novel antibody molecules which bind i) the IIICS isoform of fibronectin, ii) matrix-metalloproteinase 3 (MMP3), iii) periostin, or iv) tenascin-W, and have shown that these antibody molecules are capable of targeting vascular structures, including the neovasculature of tumour tissues and neovasculature associated with inflammatory disorders, such as rheumatoid arthritis (RA). These antibody molecules can thus be used for the targeted delivery of therapeutic and/or diagnostic agents to the neovasculature for which there is a continued need.

In a first aspect, the present invention relates to an antibody molecule that binds the IIICS isoform of fibronectin. Preferably, the antibody molecule binds the IIICS domain of fibronectin. More preferably, the antibody molecule binds the 89V splice-isoform and/or the 120V splice-isoform of the IIICS domain of fibronectin (see FIG. 1). The fibronectin is preferably human fibronectin. The antibody molecule may comprise the VH domain complementary determining region 3 (HCDR3) of the SW01 antibody molecule set forth in SEQ ID NO: 5, or an HCDR3 with the amino acid sequence set forth in SEQ ID NO: 5 with three or fewer amino acid substitutions, deletions, or insertions. In addition, the antibody molecule may comprise the HCDR1, HCDR2, LCDR1, LCDR2, and/or LCDR3 sequences of the SW01 antibody molecule set forth in SEQ ID NOs 3-4 and 6-8. For example, the antibody molecule may comprise the VH domain and/or VL domain of the SW01 antibody molecule set forth in SEQ ID NOs 1 and 2, respectively. Alternatively, the antibody molecule may comprise the HCDR3 of antibody molecule SW02 set forth in SEQ ID NO: 13, or an HCDR3 with the amino acid sequence set forth in SEQ ID NO: 13 with three or fewer amino acid substitutions, deletions, or insertions. In addition, the antibody molecule may comprise the HCDR1, HCDR2, LCDR1, LCDR2, and/or LCDR3 sequences of the SW02 antibody molecule set forth in SEQ ID NOs 11-12 and 14-16. For example, the antibody molecule may comprise the VH domain and/or VL domain of the SW02 antibody molecule set forth in SEQ ID NOs 9 and 10, respectively.

In a second aspect, the present invention relates to an antibody molecule that binds matrix-metalloproteinase 3 (MMP3). Preferably, the antibody molecule binds to the catalytic domain of MMP3. The MMP3 is preferably human MMP3. The antibody molecule preferably comprises the HCDR3 of the CH01 antibody molecule set forth in SEQ ID NO: 21, or an HCDR3 with the amino acid sequence set forth in SEQ ID NO: 21 with three or fewer amino acid substitutions, deletions, or insertions. In addition, the antibody molecule may comprise the HCDR1, HCDR2, LCDR1, LCDR2, and/or LCDR3 sequences of the CH01 antibody molecule set forth in SEQ ID NOs 19-20 and 22-24. For example, the antibody molecule may comprise the VH domain and/or VL domain of the CH01 antibody molecule set forth in SEQ ID NOs 17 and 18, respectively.

In a third aspect, the present invention relates to an antibody molecule that binds periostin. Preferably, the antibody molecule binds to FAS domains 1-4 of periostin. The periostin is preferably human periostin. Periostin is also known as Osteoblast Specific Factor 2 (OSF-2). The antibody molecule may comprise the HCDR3 of the LG1 antibody molecule set forth in SEQ ID NO: 29, or an HCDR3 with the amino acid sequence set forth in SEQ ID NO: 29 with three or fewer amino acid substitutions, deletions, or insertions. In addition, the antibody molecule may comprise the HCDR1, HCDR2, LCDR1, LCDR2, and/or LCDR3 sequences of the LG1 antibody molecule set forth in SEQ ID NOs 27-28 and 30-32. For example, the antibody molecule may comprise the VH domain and/or VL domain of the LG1 antibody molecule set forth in SEQ ID NOs 25 and 26, respectively. Alternatively, the antibody molecule may comprise the HCDR3 of antibody molecule LG2 set forth in SEQ ID NO: 37, or an HCDR3 with the amino acid sequence set forth in SEQ ID NO: 37 with three or fewer amino acid substitutions, deletions, or insertions. In addition, the antibody molecule may comprise the HCDR1, HCDR2, LCDR1, LCDR2, and/or LCDR3 sequences of the LG2 antibody molecule set forth in SEQ ID NOs 35-36 and 38-40. For example, the antibody molecule may comprise the VH domain and/or VL domain of the LG2 antibody molecule set forth in SEQ ID NOs 33 and 34, respectively. As a further alternative, the antibody molecule may comprise the HCDR3 of antibody molecule LG3 set forth in SEQ ID NO: 45, or an HCDR3 with the amino acid sequence set forth in SEQ ID NO: 45 with three or fewer amino acid substitutions, deletions, or insertions. In addition, the antibody molecule may comprise the HCDR1, HCDR2, LCDR1, LCDR2, and/or LCDR3 sequences of the LG3 antibody molecule set forth in SEQ ID NOs 43-44 and 46-48. For example, the antibody molecule may comprise the VH domain and/or VL domain of the LG3 antibody molecule set forth in SEQ ID NOs 41 and 42, respectively. As a yet further alternative, the antibody molecule may comprise the HCDR3 of antibody molecule 1E1 set forth in SEQ ID NO: 53, or an HCDR3 with the amino acid sequence set forth in SEQ ID NO: 53 with three or fewer amino acid substitutions, deletions, or insertions. In addition, the antibody molecule may comprise the HCDR1, HCDR2, LCDR1, LCDR2, and/or LCDR3 sequences of the 1E1 antibody molecule set forth in SEQ ID NOs 51-52 and 54-56. For example, the antibody molecule may comprise the VH domain and/or VL domain of the 1E1 antibody molecule set forth in SEQ ID NOs 49 and 50, respectively.

In a fourth aspect, the present invention relates to an antibody molecule that binds tenascin-W. The tenascin-W is preferably human tenascin-W. The antibody molecule preferably comprises the HCDR3 of the G10 antibody molecule set forth in SEQ ID NO: 61, or an HCDR3 with the amino acid sequence set forth in SEQ ID NO: 61 with three or fewer amino acid substitutions, deletions, or insertions. In addition, the antibody molecule may comprise the HCDR1, HCDR2, LCDR1, LCDR2, and/or LCDR3 sequences of the G10 antibody molecule set forth in SEQ ID NOs 59-60 and 62-64. For example, the antibody molecule may comprise the VH domain and/or VL domain of the SW01 antibody molecule set forth in SEQ ID NOs 57 and 58, respectively. Optionally the residue at position 67 of SEQ ID NO 57 may be an arginine (R) instead of a Glutamine (Q).

As mentioned above, an antibody molecule of the invention may comprise a HCDR3 sequence as disclosed herein with three or fewer amino acid substitutions, deletions, or insertions. For example, an antibody molecule of the invention may comprise a HCDR3 sequence as disclosed herein with two or fewer, or one, amino acid substitution(s), deletion(s), or insertion(s). As with regard to the HCDR3 sequences, an antibody molecule of the invention may comprise a HCDR1, HCDR2, LCDR1, LCDR2, and/or LCDR3 sequence, as disclosed herein, with three or fewer, two or fewer, or one, amino acid substitution(s), deletion(s), or insertion(s). Similarly, and antibody molecule of the invention may comprise a VH and/or VL domain sequence as disclosed with ten or fewer, e.g. nine or fewer, eight or fewer, seven or fewer, six or fewer, five or fewer, four or fewer, three or fewer, two or fewer, or one, amino acid substitution(s), deletion(s), or insertion(s).

An antibody molecule, as referred to herein, may be in any suitable format. Many antibody molecule formats are known in the art and include both complete antibody molecule molecules, such as IgG, as well as antibody molecule fragments, such as a single chain Fv (scFv). The term "antibody molecule" as used herein encompasses both complete antibody molecule molecules and antibody molecule fragments, in particular antigen-binding fragments. Preferably, an antibody molecule comprises a VH domain and a VL domain. In a preferred embodiment, the antibody molecule is or comprises a scFv, is a small immunoprotein (SIP), is a diabody, or is a (complete) IgG molecule.

An antibody molecule of the present invention may be conjugated to a molecule to provide a conjugate. The choice of molecule conjugated to the antibody molecule will depend on the intended application of the conjugate. For example, where the conjugate is intended for the treatment of a disease or disorder, the conjugate may comprise an antibody molecule of the invention and a biocidal molecule, a cytotoxic molecule, a radioisotope, a photosensitizer, an enzyme, a hormone, an anti-inflammatory agent, or a cytokine. Where the conjugate is intended for use in imaging, detecting, or diagnosing a disease or disorder, the conjugate may comprise an antibody molecule of the invention and a detectable label, such as a radioisotope, e.g. a non-therapeutic radioisotope. Depending on the molecule conjugated to the antibody molecule, the conjugate may be or may comprise a single chain protein. When the conjugate is a single chain protein, the entire protein can be expressed as a single polypeptide or fusion protein. In this case, the molecule may be conjugated to the antibody molecule by means of a peptide linker. Fusion proteins have the advantage of being easier to produce and purify since they consist of one single species. This facilitates production of clinical-grade material. Alternatively, the molecule may be conjugated to the antibody molecule by means of a cleavable linker.

The invention also provides isolated nucleic acids encoding the antibodies and conjugates of the invention. The skilled person would have no difficulty in preparing such nucleic acids using methods well-known in the art. An isolated nucleic acid may be used to express the antibody molecule or conjugate of the invention, for example by expression in a bacterial, yeast, insect or mammalian host cell. A preferred host cell is *E. coli*. The nucleic acid will generally be provided in the form of a recombinant vector for expression. Host cells in vitro comprising such vectors are part of the invention, as is their use for expressing the antibodies and conjugates of the invention, which may subsequently be purified from cell culture and optionally formulated into a pharmaceutical composition.

An antibody molecule or conjugate of the invention may be provided for example in a pharmaceutical composition, and may be employed for medical use as described herein, either alone or in combination with one or more further therapeutic agents. Alternatively, the antibody molecule or conjugate of the invention may be provided in a diagnostic composition and may be employed for diagnostic use as described herein.

In a fifth aspect, the invention relates to an antibody molecule or conjugate of the invention for use in a method for treatment of the human or animal body by therapy. For example, an antibody molecule or conjugate of the invention may for use in a method of treating an inflammatory disorder, inhibiting angiogenesis, treating cancer, and/or treating an autoimmune disease in a patient. The invention also relates to a method of treating an inflammatory disorder, inhibiting angiogenesis, treating cancer, and/or treating an autoimmune disease in a patient, the method comprising administering a therapeutically effective amount of an antibody molecule or conjugate of the invention to the patient.

In a sixth aspect, the invention relates to an antibody molecule of the invention for use in a method of delivering a molecule to sites of an inflammatory disorder, sites of neovasculature which are the result of angiogenesis, sites of cancer and/or sites of autoimmune disease in a patient. The invention also relates to a method of delivering a molecule to sites of an inflammatory disorder, sites of neovasculature which are the result of angiogenesis, sites of cancer and/or sites of autoimmune disease in a patient comprising administering to the patient an antibody molecule of the invention, wherein the antibody molecule is conjugated to the molecule.

In a seventh aspect, the invention relates to an antibody molecule or conjugate of the invention for use in a method of imaging, detecting, or diagnosing an inflammatory disorder, angiogenesis, cancer, and/or an autoimmune disease in a patient. The invention further relates to a method of imaging, detecting, or diagnosing an inflammatory disorder, angiogenesis, cancer, and/or an autoimmune disease in a patient comprising administering an antibody molecule or conjugate of the invention to the patient.

A patient, as referred to herein, is preferably a human patient.

DETAILED DESCRIPTION

Figure 1:
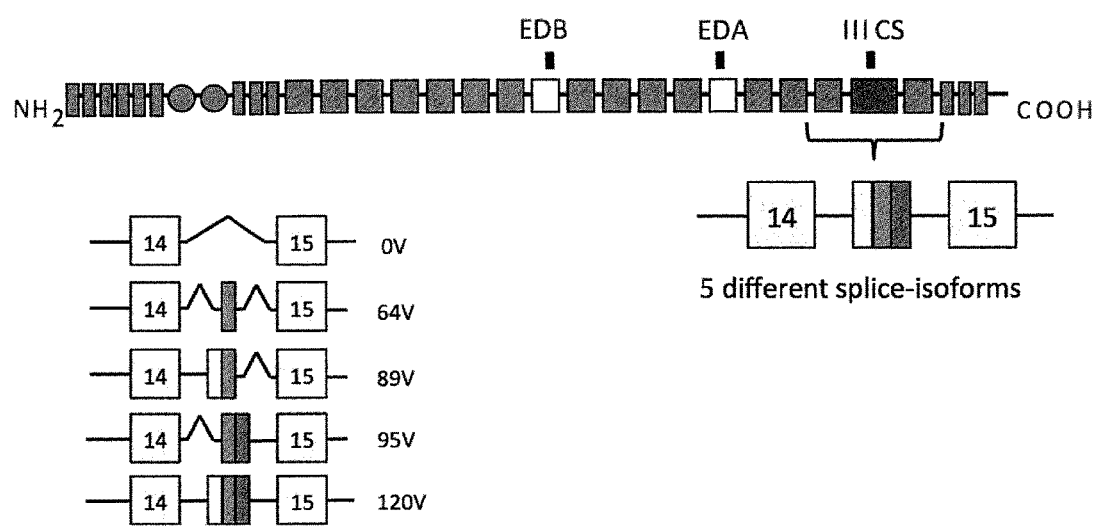
FIG. 1 is schematic diagram showing the 5 possible splice isoforms of the IIICS isoform of fibronectin.

The invention includes the combination of the aspects and preferred features described except where such a combination is clearly impermissible or expressly avoided.

In one aspect, the present invention relates to an antibody which binds i) the IIICS isoform of fibronectin, ii) matrix-metalloproteinase 3 (MMP3), iii) periostin, or iv) tenascin-W).

Antibody Molecule

The term "antibody molecule" describes an immunoglobulin whether natural or partly or wholly synthetically produced. The term also covers any polypeptide or protein having a binding domain which is, or is substantially homologous to, an antibody binding domain. Examples of antibodies are the immunoglobulin isotypes and their isotypic subclasses; fragments which comprise an antigen binding domain such single chain diabodies. The antibody molecule or fragment thereof may be human or humanised. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody molecule" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

The term "specific" may be used to refer to the situation in which the antibody molecule will not show any significant binding to molecules other than its specific binding partner(s). The term is also applicable where e.g. an antigen-binding site of an antibody molecule is specific for a particular epitope that is carried by a number of antigens, in which case the antibody molecule carrying the antigen-binding site will be able to bind to the various antigens carrying the epitope.

The antibody molecule may be monovalent or bivalent i.e. may have two antigen binding sites. Where the antibody molecule is bivalent, the two antigen binding sites may be identical or different. An "antigen binding site" describes the part of an antibody which comprises the area which specifically binds to and is complementary to part or all of an antigen. Where an antigen is large, an antibody molecule may only bind to a particular part of the antigen, which part is termed an epitope. An antigen binding site may be provided by one or more antibody variable domains (e.g. a so-called Fd antibody fragment consisting of a VH domain). Preferably, an antigen binding site comprises an antibody light chain variable region (VL) and an antibody heavy chain variable region (VH).

An antibody molecule of the invention preferably comprises the HCDR3 of antibody SW01, antibody SW02, antibody CH01, antibody LG1, antibody LG2, antibody LG3, antibody 1E1, or antibody G10. The HCDR3 is known to play a role in determining the specificity of an antibody molecule (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144:4863-4869; Kabat et al., (1991b), J. Immunol., 147:1709-1719).

The antibody molecule may further comprise the HCDR1, HCDR2, LCDR1, LCDR2 and/or LCDR3 of antibody SW01, antibody SW02, antibody CH01, antibody LG1, antibody LG2, antibody LG3, antibody 1E1, or antibody G10.

The antibody may also comprise the VH and/or VL domain of antibody SW01, antibody SW02, antibody CH01, antibody LG1, antibody LG2, antibody LG3, antibody 1E1, or antibody G10.

An antibody molecule of the invention may have a VH domain having at least 70%, more preferably one of at least 75%, 80%, 85%, 90%, 95%, 96%, 97%, 98%, 99% or 100%, sequence identity to the VH domain of antibody SW01, antibody SW02, antibody CH01, antibody LG1, antibody LG2, antibody LG3, antibody 1E1, or antibody G10.

An antibody molecule of the invention may have a VL domain having at least 70%, more preferably one of at least 75%, 80%, 85%, 90%, 95%, 96%, 97%, 98%, 99% or 100%, sequence identity to the VL domain of antibody SW01, antibody SW02, antibody CH01, antibody LG1, antibody LG2, antibody LG3, antibody 1E1, or antibody G10.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

Variants of these VH and VL domains and CDRs may also be employed in antibody molecules for use in as described herein. Suitable variants can be obtained by means of methods of sequence alteration, or mutation, and screening.

Particular variants for use as described herein may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1.

Alterations may be made in one or more framework regions and/or one or more CDRs. In particular, alterations may be made in HCDR1, HCDR2 and/or HCDR3.

The antibody molecule may be a whole antibody or a fragment thereof, in particular an antigen-binding fragment thereof.

Whole antibodies include IgA, IgD, IgE, IgG or IgM. Preferably, the whole antibody is IgG.

Antigen-binding fragments of whole antibodies include (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-554; Holt et al. (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO2013/014149; WO94/13804; Holliger et al. (1993a), Proc. Natl. Acad. Sci. USA 90 6444-6448). Fv, scFv or diabody molecules may be stabilized by the incorporation of disulphide bridges linking the VH and VL domains (Reiter et al. (1996), Nature Biotech, 14, 1239-1245). Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

A single chain Fv (scFv) may be comprised within a mini-immunoglobulin or small immunoprotein (SIP), e.g. as described in (Li et al., (1997), Protein Engineering, 10: 731-736). An SIP may comprise an scFv molecule fused to the CH4 domain of the human IgE secretory isoform IgE-S2 ($\varepsilon_{S2}$-CH4; Batista et al., (1996), J. Exp. Med., 184: 2197-205) forming an homo-dimeric mini-immunoglobulin antibody molecule Preferably the antibody molecule comprises or consists of a single chain Fv, a small immunoprotein, a diabody, or a (whole) IgG molecule.

Conjugates

Conjugates of the invention comprise an antibody molecule of the invention and a therapeutic or diagnostic agent. The therapeutic agent may be a biocidal molecule, a cytotoxic molecule, a radioisotope, a photosensitizer, an enzyme, a hormone, or an anti-inflammatory agent. Preferably, the therapeutic agent is a biocidal molecule, a cytotoxic molecule, a radioisotope, or an anti-inflammatory agent. The biocidal molecule, cytotoxic molecule, or anti-inflammatory agent may be a cytokine.

The diagnostic agent may be radioisotope, e.g. a non-therapeutic radioisotope.

Radioisotopes which may be conjugated to a binding member of the invention include isotopes such as $^{94m}$Tc, $^{99m}$Tc, $^{186}$Re, $^{188}$Re, $^{203}$Pb, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Lu, $^{123}$I, $^{124}$I, $^{125}$I, $^{131}$I, $^{18}$F, $^{211}$At and $^{225}$Ac. Preferably, positron emitters, such as $^{18}$F and $^{124}$I, or gamma emitters, such as $^{99m}$Tc, $^{111}$In and $^{123}$I, are used for diagnostic applications (e.g. for PET), while beta-emitters, such as $^{131}$I, $^{90}$Y and $^{177}$Lu, are preferably used for therapeutic applications. Alpha-emitters, such as $^{211}$At and $^{225}$Ac may also be used for therapy. In one example, the specific binding member may be conjugated to $^{177}$Lu or $^{90}$Y.

The specific binding member may be conjugated with the therapeutic agent by means of a peptide bond or linker, i.e. within a fusion polypeptide comprising said molecule and the specific binding member or a polypeptide chain component thereof. Other means for conjugation include chemical conjugation, especially cross-linking using a bifunctional reagent (e.g. employing DOUBLE-REAGENTS™ Cross-linking Reagents Selection Guide, Pierce).

Linkers

The antibody molecule and the therapeutic or diagnostic agent may be connected to each other directly, for example through any suitable chemical bond or through a linker, for example a peptide linker.

The peptide linker may be a short (2-20, preferably 2-15, residue stretch of amino acids). Suitable examples of peptide linker sequences are known in the art. One or more different linkers may be used. The linker may be about 5 amino acids in length.

The chemical bond may be, for example, a covalent or ionic bond. Examples of covalent bonds include peptide bonds (amide bonds) and disulphide bonds. For example the antibody molecule and therapeutic or diagnostic agent may be covalently linked. For example by peptide bonds (amide bonds). Thus, the antibody molecule and therapeutic or diagnostic agent may be produced (secreted) as a single chain polypeptide. The individual components that form the antibody molecule or the therapeutic or diagnostic agent may also be connected directly, for example through any suitable chemical bond, or through a linker, for example a peptide linker. Examples of individual components which may be linked within the antibody molecule are CDRs or VH or VL sequences.

Methods of Treatment and Diagnosis

An antibody molecule or conjugate of the invention may be used in a method of treatment of the human or animal body, such as a method of treatment (which may include prophylactic treatment) of a disease or disorder in a patient (typically a human patient) comprising administering the antibody molecule or conjugate to the patient.

Accordingly, such aspects of the invention provide methods of treatment comprising administering an antibody molecule or conjugate of the invention, pharmaceutical compositions comprising such an antibody molecule or conjugate for the treatment of a condition or disease, and a method of making a medicament or pharmaceutical composition comprising formulating the antibody molecule or conjugate of the present invention with a physiologically acceptable carrier or excipient.

An antibody molecule or conjugate as herein described may be used in a method of treating an inflammatory disorder, inhibiting angiogenesis, treating cancer, and/or treating an autoimmune disease in a patient. The method may comprise targeting a therapeutic agent to the neovasculature in vivo. The agent may be any therapeutic agent discussed herein, which is suitable for treatment of the disease or disorder in question.

Also contemplated is a method of treating an inflammatory disorder, inhibiting angiogenesis, treating cancer, and/or treating an autoimmune disease in a patient by targeting a therapeutic agent to the neovasculature in a patient, the method comprising administering a therapeutically effective amount of an antibody molecule or conjugate as herein described to the patient.

An antibody molecule or conjugate as herein described may also be used in a method of imaging, detecting, or diagnosing a disease or disorder in a patient. A method of imaging, detecting, or diagnosing a disease or disorder comprising administering an antibody or conjugate as described herein to a patient is similarly contemplated. The disease or disorder may be an inflammatory disorder, angiogenesis, cancer, and/or an autoimmune disease. The method may comprise targeting a diagnostic agent, such as a detectable label, to the neovasculature in vivo.

Inflammatory disorders include any disease or disorder which is characterised by an inflammatory abnormality.

Such disease include, for example, immune system disorders, such as autoimmune diseases, and cancer.

Angiogenesis is a feature of many known diseases and disorders and inhibition of angiogenesis using an antibody or conjugate of the invention may be used to treat such diseases and disorders. Similarly, diseases and disorders characterised by angiogenesis may be imaged, detected, or diagnosed using an antibody or conjugate described herein. Disease characterised by angiogenesis include, for example, rheumatoid arthritis, diabetic retinopathy, age-related muscular degeneration, angiomas, tumours and cancer.

As mentioned above, conditions which may be treated, imaged, detected, or diagnosed using an antibody or conjugate as described herein include cancer, as well as other tumours and neoplastic conditions.

Exemplary cancers include any type of solid or non-solid cancer or malignant lymphoma and especially liver cancer, lymphoma, leukaemia (e.g. acute myeloid leukaemia), sarcomas, skin cancer, bladder cancer, breast cancer, uterine cancer, ovarian cancer, prostate cancer, lung cancer, colorectal cancer, cervical cancer, head and neck cancer, oesophageal cancer, pancreatic cancer, renal cancer, stomach cancer and cerebral cancer. Cancers may be familial or sporadic. Cancers may be metastatic or non-metastatic. The cancer, tumour, or neoplastic condition may express i) the IIICS isoform of fibronectin, ii) matrix-metalloproteinase 3 (MMP3), iii) periostin, and/or iv) tenascin-W.

Autoimmune disease which may be treated, imaged, detected, or diagnosed using an antibody or conjugate as described herein include lupus erytematosus, rheumatoid arthritis, and psoriathic arthritis.

A further disease or disorder which may treated, imaged, detected, or diagnosed using an antibody or conjugate described herein is osteoarthritis.

Pharmaceutical Compositions

A further aspect of the present invention relates to a pharmaceutical composition comprising at least one antibody molecule or conjugate of the invention and optionally a pharmaceutically acceptable excipient.

Pharmaceutical compositions of the present invention typically comprise a therapeutically effective amount of an antibody molecule or conjugate according to the invention and optionally auxiliary substances such as pharmaceutically acceptable excipient(s). Said pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilisers, antioxidants, pH-regulating substances, controlled-release excipients. The pharmaceutical composition of the invention may be adapted, for example, for parenteral use and may be administered to the patient in the form of solutions or the like.

Pharmaceutical compositions comprising the antibody molecule or conjugate of the present invention may be administered to a patient. Administration is preferably in a "therapeutically effective amount", this being sufficient to show benefit to the patient. Such benefit may be amelioration of at least one symptom. The actual amount administered, and rate and time-course of administration, will depend on the nature and severity of what is being treated. Prescription of treatment, e.g. decisions on dosage etc., is within the responsibility of general practitioners and other medical doctors. Treatments may be repeated at daily, twice-weekly, weekly, or monthly intervals at the discretion of the physician.

A pharmaceutical composition of the invention may be administered to a patient in need of treatment via any suitable route, usually by injection into the bloodstream and/or directly into the site to be treated. The precise dose and its frequency of administration will depend upon a number of factors, the route of treatment, the size and location of the area to be treated.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included For intravenous injection, or injection at the site of affliction, the pharmaceutical composition will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A pharmaceutical composition may be administered alone or in combination with other treatments, either simultaneously or sequentially dependent upon the condition to be treated.

Kits

Another aspect of the invention provides a therapeutic kit for use in the treatment of a disease or disorder comprising an antibody molecule or conjugate as described herein. The components of a kit are preferably sterile and in sealed vials or other containers.

A kit may further comprise instructions for use of the components in a method described herein. The components of the kit may be comprised or packaged in a container, for example a bag, box, jar, tin or blister pack.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1

Preparation and Characterisation of Two New Antibodies Against the IIICS Isoform of Fibronectin Antibodies SW01 and SW02 were isolated in single-chain Fv (scFv) configuration from phage display libraries which include the libraries described in PCT/EP2009/006487, in Weber et al. (PLoS One, 2014, 9 (6) doi: 10/1361) and in Silacci et al. (Protein Engineering Design & Selection, 2006, 19, 471-478) according to the screening technique described by Silacci et al. (Protein Engineering Design & Selection, 2006, 19, 471-478) using fibronectin IIICS as the screening antigen.

The SW01 and SW02 antibodies when used in monomeric scFv format, bind to the IIICS (89V) and IIICS (120V) isoforms (FIG. 1). Furthermore, using ELISA antibodies SW01 and SW02 were shown to recognize both the human and the rat recombinant IIICS (120V) isoform.

Figure 2A:
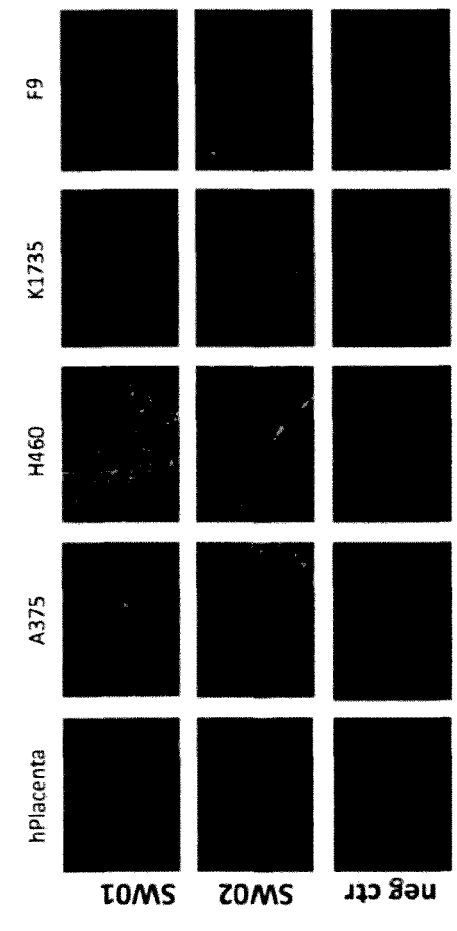
FIG. 2A shows staining of human placenta (hPlacenta), human tumours (A375 and H460) and murine tumours (K1735 and F9) with antibodies SW01 and SW02, which bind to the IIICS isoform of fibronectin, and negative control antibodies (neg. ctr). The negative control antibodies used were anti-human Von Willebrand Factor (Anti huVWF) in the human placenta experiments and anti-murine CD31 (muCD31) in the tumour experiments.

Antibodies SW01 and SW02 display good performance in immunofluorescence analyses. FIG. 2A shows staining of human placenta, human tumours (A375, H460) and murine tumours (K1735, F9) by SW01 and SW02 in SIP format. Specifically, SW01 and SW02 show distinct staining of vascular and perivascular structures in these tissues/tumours. As negative controls (neg ctr) an anti-human von Willebrand factor antibody (anti huVWF) was used for the human placenta experiments and an anti-murine CD31 antibody (muCD31) was used for the tumor experiments.

Figure 2B:
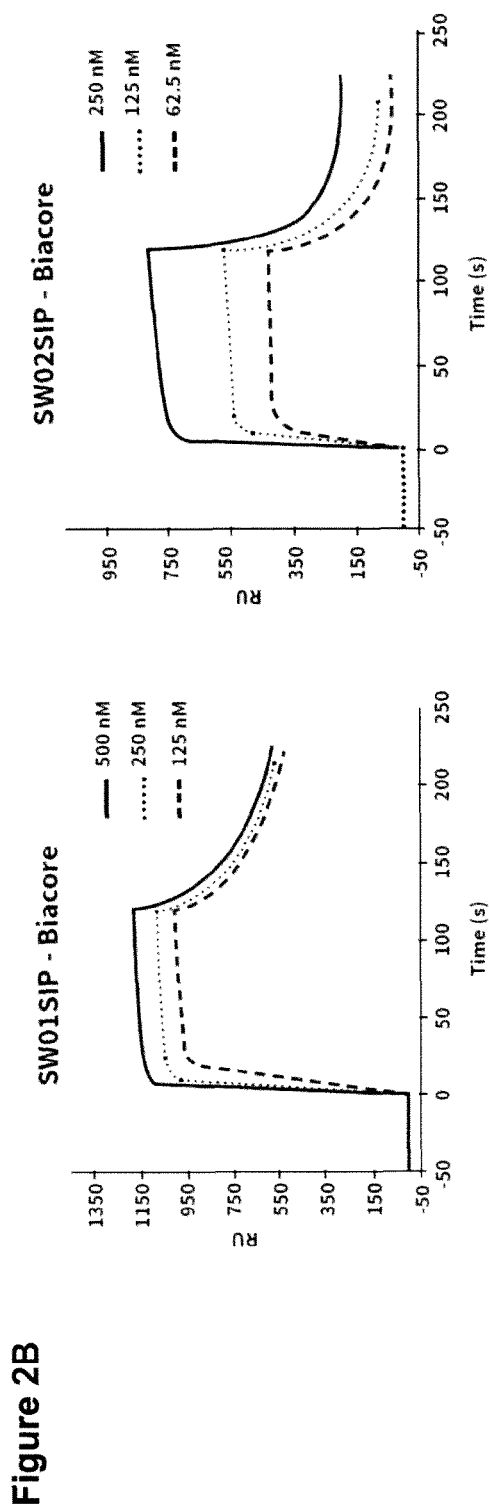
FIG. 2B shows Biacore data demonstrating binding of antibody SW01 to IIICS.

Binding of antibody SW01 and SW02 to IIICS was further confirmed by Biacore analysis. The results are shown in FIG. 2B.

Immunofluorescence on Tumour Sections:

Cryostat sections (10 µm) of tumors were fixed in ice-cold acetone, rehydrated with PBS and blocked with 20% foetal bovine serum in PBS.

The SW01 and SW02 anti-IIICS antibodies and the KSF anti-hen egg lysozyme antibodies (all in SIP format) were diluted in 3% BSA to a final concentration of 5 µg/mL and then added to the tissue sections. Rabbit-a-Human IgE antibody (Dako) and rat-a-mouse-CD31 antibody (BD Biosciences) were used for co-staining of SIP antibody fusion proteins and endothelial cells from blood vessels, respectively. Anti-Rabbit-Alexa488 and anti-Rat-Alexa594 (Invitrogen) secondary antibodies were used for detection.

Immunofluorescence on Human Placenta:

Cryostat sections (10 µm) of human placenta were fixed in ice-cold acetone, rehydrated with PBS and blocked with 20% foetal bovine serum in PBS.

The SW01 and SW02 anti-IIICS antibodies and the KSF anti-hen egg lysozyme antibody (all in SIP format) were biotinylated and diluted in 3% BSA to a final concentration of 5 µg/mL and then added to the tissue. Rabbit-anti-Human Von Willebrand antibody (Dako) was used for staining of endothelial cells from blood vessels. Anti-Rabbit-Alexa594 and Streptavidin-Alexa488 (Invitrogen) secondary antibodies were used for detection.

Biacore Analysis:

Binding of antibodies SW01 and SW02 to IIICS was further determined by Biacore analysis. A CM5 chip was coated with 14(89V)15 (a recombinant polypeptide which includes domain 14, extra domain-89V of IIICS and domain 15 of fibronectin) to achieve a final coating density of 1400 resonance units (RU). The SW01 and SW02 antibodies produced in SIP format were diluted in 30 mM $Na_2HPO_4$, 20 mM $NaH_2PO_4$, 100 mM NaCl pH 7.4 to provide solutions with the following concentrations:

1) SIP(SW01): 500 nM, 250 nM, and 125 nM
2) SIP(SW02): 250 nM, 125 nM, and 62.5 nM The flow rate for the Biacore analysis was set at 10 µL/min. 10 µL of each antibody sample were injected into the system. Analysis was performed in HBS-EP buffer. After each injection, the chip was regenerated by the injection of 5 µL of 10 mM HCl.

Example 2

Preparation and Characterisation of a New Antibody Against MMP3

The CH01 antibody was isolated in scFv configuration from phage display libraries which include the libraries described in PCT/EP2009/006487, in Weber et al. (PLoS One, 2014, 9 (6) doi: 10/1361) and in Silacci et al. (Protein Engineering Design & Selection, 2006, 19, 471-478) according to the screening technique described by Silacci et al. (Protein Engineering Design & Selection, 2006, 19, 471-478) using a recombinant version of the catalytic domain of human MMP3 (amino acids 100-273). The antigen was produced in a bacterial expression system and biotinylated according to the standard protocol.

Figure 3:
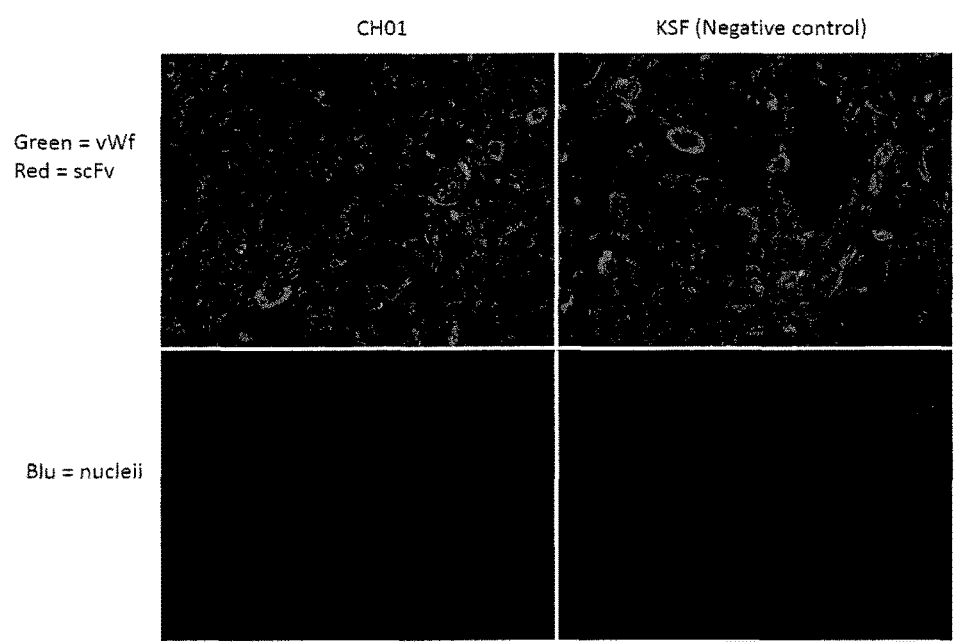
FIG. 3 shows staining of human placenta using the anti-human MMP3 antibody CH01 in scFv format. The anti-hen egg lysozyme antibody KSF in scFv format was used as a negative control. Staining by the two scFv antibodies is shown in red, staining with the vascular marker human Von Willebrand factor is shown in green and nucleii were stained in blue using DAPI.

Antibody CH01 displays good staining of neovascular structures as shown by Immunofluorescence analyses. FIG. 3 shows staining of human placenta samples, in which 10 µm thick tissue samples were stained with the anti-human MMP3 antibody CH01 in scFv format. The anti-hen egg lysozyme antibody KSF in scFv format was used as an isotype-negative control for the staining. ScFv staining is shown in red, the vascular marker human Von Willebrand factor is shown in green and nucleii were stained in blue using DAPI. Unlike the negative control, the CH01 antibody stains neovascular structures in the placenta specimens.

Figure 4A:
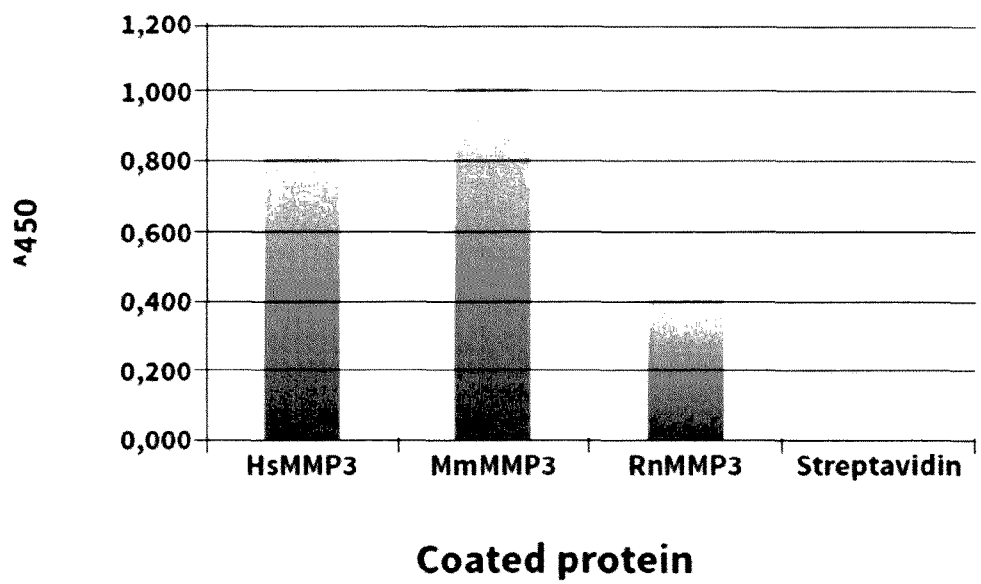
FIG. 4A shows the ability of anti-human MMP3 antibody CH01 to bind to the biotinylated catalytic domains of human (HsMMP3), mouse (MmMMP3) and rat (RnMMP3) MMP3 in an ELISA. CH01 recognizes both human and mouse MMP3 and to a lesser extent rat MMP3.

The cross-reactivity of the CH01 antibody for the MMP3 of different species was analysed by determining binding of the CH01 antibody to the biotinylated catalytic domains of human, mouse and rat MMP3 in an ELISA. The results shown in FIG. 4A, indicate that CH01 recognize both mouse and human MMP3 and to a lesser extent rat MMP3.

Figure 4B:
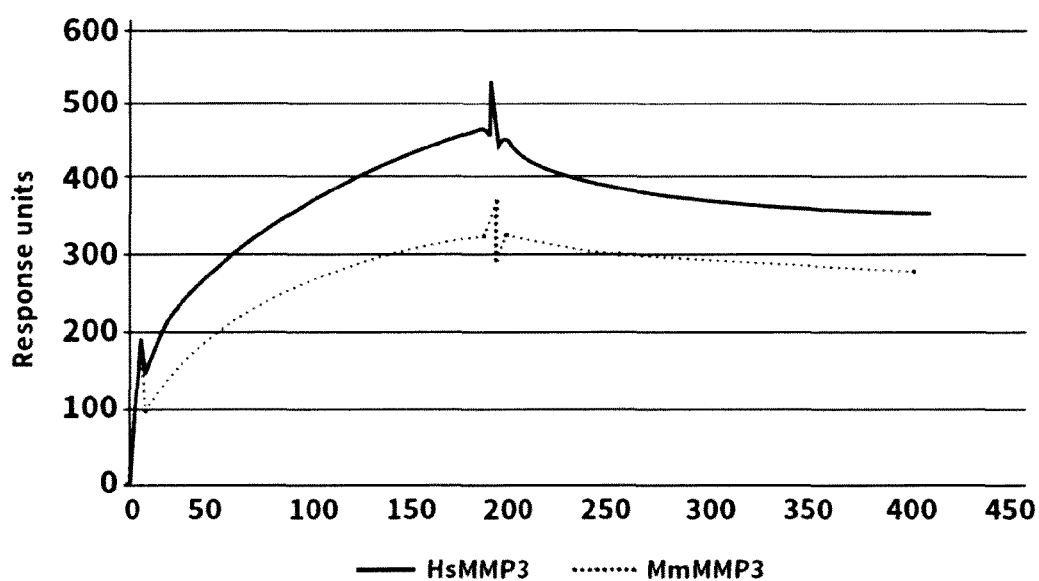
FIG. 4B shows Biacore data demonstrating binding of antibody CH01 to human and mouse MMP3.

Binding of antibody CH01 to the catalytic domain of human and mouse MMP3 was also confirmed by Biacore analysis. The results are shown in FIG. 4B.

Immunofluorescence on Human Placenta Samples:

Dual staining for MMP3 and von Willebrand factor (vWF, an endothelial marker) was performed on human placenta samples. 10 µm thick frozen specimens were defrosted at room temperate and treated with ice-cold acetone, rehydrated in PBS and blocked with 3% BSA. Affinity-purified myc-tagged scFv antibodies (final concentration 5 mg/ml) were first incubated with the tissue sample, followed by the biotinylated monoclonal anti-myc 9E10 antibody (5 mg/ml) and the endothelial marker antibody. Bound scFvs were detected with Strepavidin Alexa 594 (Molecular Probes). The anti-vWF antibody (DAKO) was detected using goat anti-rabbit IgG Alexa 488. DAPI was used for nuclei staining. The anti-hen egg lysozyme antibody scFv(KSF) was used as an isotype-negative control for the staining.

Cross-reactivity ELISA:

Streptawell High Bind strips (Roche) were coated with biotinylated Human, Mouse or Rat MMP3 catalytic domain at 100 nM. ScFv fragments were incubated for 1 hour, bound antibody was detected with the anti-Myc antibody 9E10 and an HRP-conjugated anti-Murine $F_c$ antibody (Sigma). The plate coating density was assessed by detecting the MMP3 catalytic domains using an HRP-conjugated anti-6×His antibody (Sigma). Colorimetric detection of antibody-antigen binding was performed using BM-Blue POD soluble substrate (Roche).

Biacore Analysis:

Purified CH01 in scFv format was injected over a CM5 chip coated with both human and mouse MMP3 catalytic domains. Response units were normalised to give a baseline value of zero. Samples were injected at a flow rate of 10 μL/min in 50 mM Tris-HCl pH 7.4, 200 mM NaCl, 1 mM CaCl₂.

Example 3

Preparation and Characterisation of Four New Antibodies Against Periostin

Figure 5:
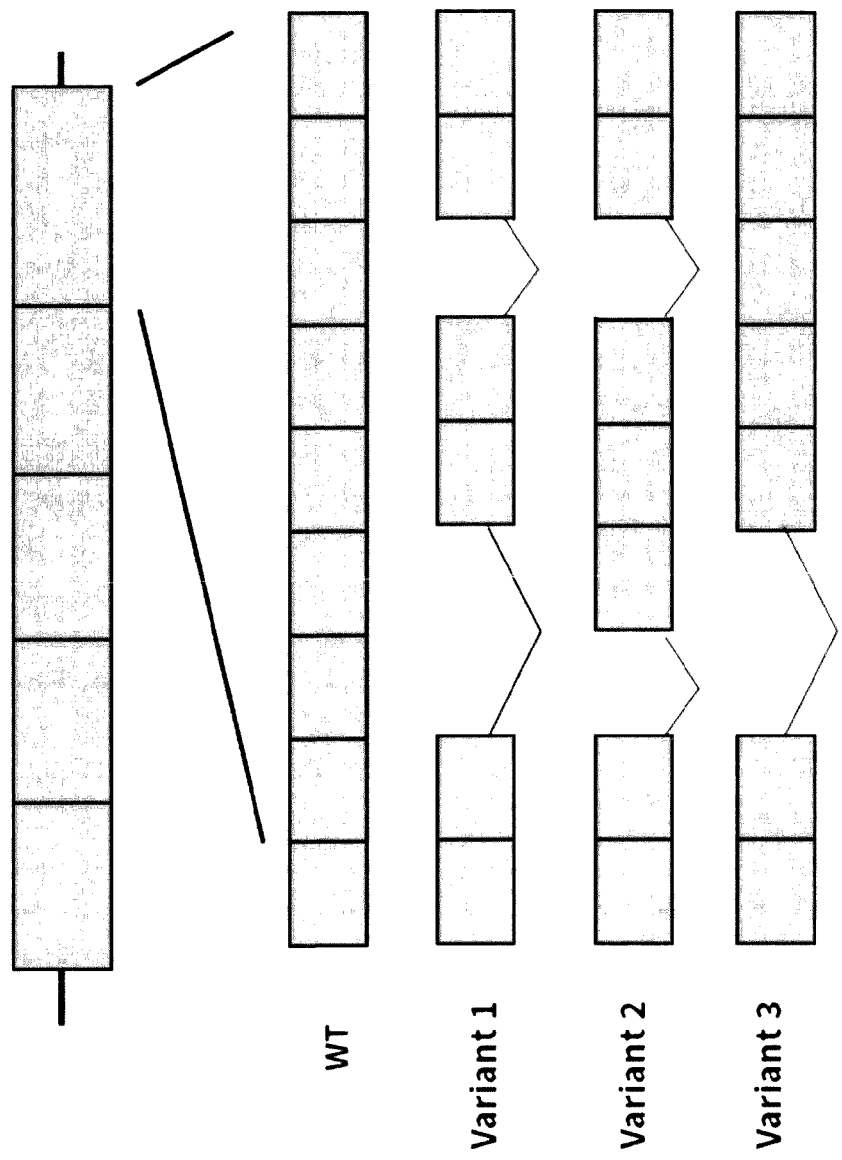
FIG. 5 is a schematic diagram showing four known isoforms of periostin.

The LG1, LG2, LG3 and 1E1 antibodies were isolated in scFv configuration from phage display libraries which include the libraries described in PCT/EP2009/006487, in Weber et al. (PLoS One, 2014, 9 (6) doi: 10/1361) and in Silacci et al. (Protein Engineering Design & Selection, 2006, 19, 471-478) according to the screening technique described by Silacci et al. (Protein Engineering Design & Selection, 2006, 19, 471-478). To generate antibodies against periostin, a recombinant version of the FAS domains (from 1 to 4; FIG. 5) was produced in a mammalian cell expression system. The antigen was biotinylated according to the standard protocol.

Figures 6A, 6B:
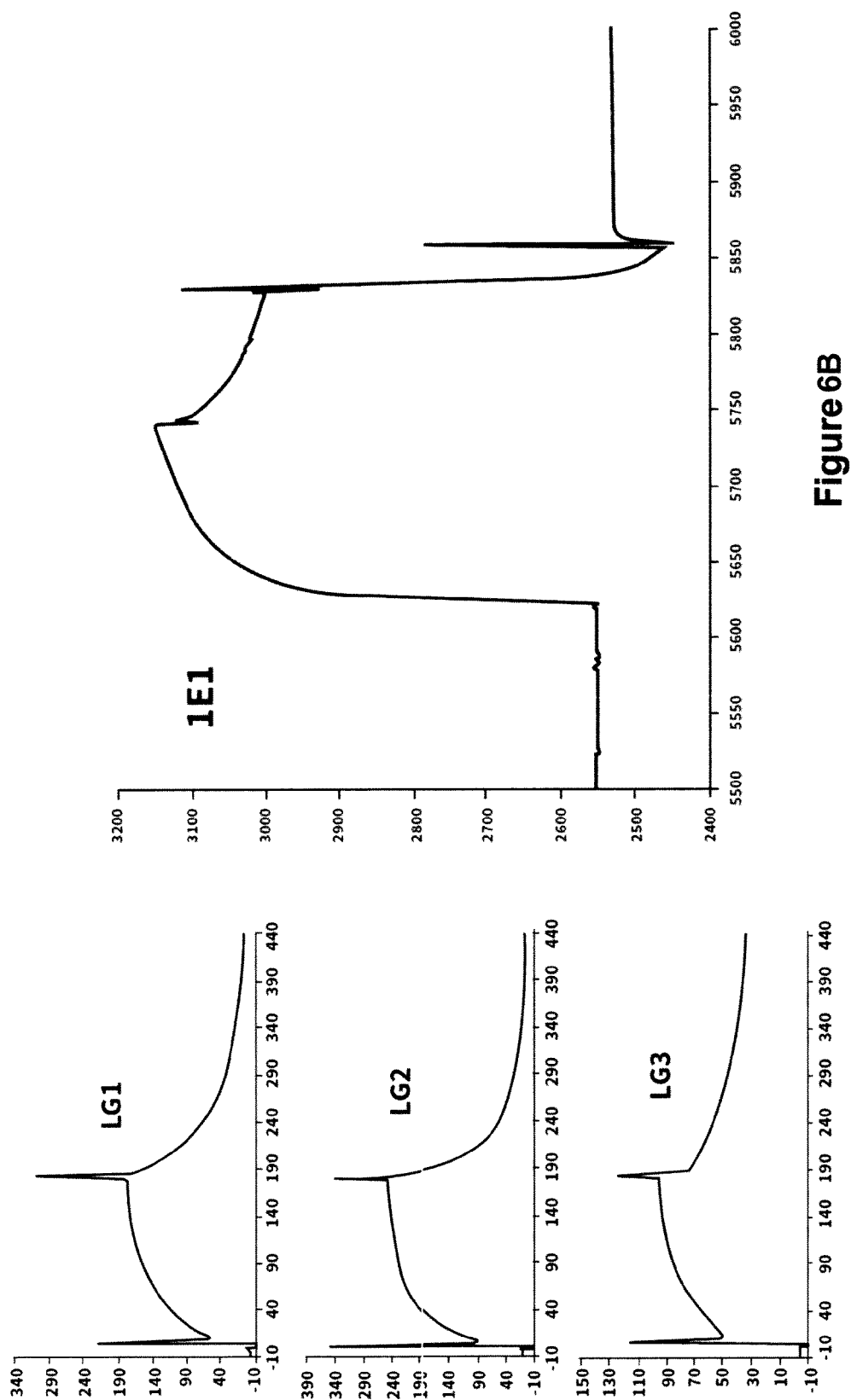
FIG. 6A shows Biacore data demonstrating binding of antibodies LG1, LG2 and LG3 (in scFv format) to periostin.
FIG. 6B shows Biacore data demonstrating binding of antibody 1E1 (in SIP format) to periostin.

Binding of antibodies LG1, LG2 and LG3 (in scFv format) and 1E1 (in SIP format) to periostin was confirmed by Biacore analysis. The results are shown in FIGS. 6A and 6B.

Biacore Analysis:

Monomeric fractions of purified antibodies were analyzed by surface plasmon resonance (BIAcore, 3000 system). Recombinant Human Periostin was covalently coupled to the surface of the CM-3 sensor Chip. Thirty microliters of each sample were injected at the flow rate of 10 μL/min. The regeneration of the chip was performed with 5 μL of 10 mM HCl.

Example 4

Preparation and Characterisation of a New Antibody Against Tenascin-W

The G10 antibody was isolated in scFv configuration from phage display libraries which include the libraries described in PCT/EP2009/006487, in Weber et al. (PLoS One, 2014, 9 (6) doi: 10/1361) and in Silacci et al. (Protein Engineering Design & Selection, 2006, 19, 471-478) according to the screening technique described by Silacci et al. (Protein Engineering Design & Selection, 2006, 19, 471-478). The G10 antibody was isolated by screening the libraries against a recombinant fragment corresponding to residues 262-534 (numbering including the leader sequence) of human tenascin-W. The recombinant fragment also contained an N-terminal Methionine and a C-terminal His6 tag. The sequence of this peptide is shown in SEQ ID NO: 65.

Figure 7:
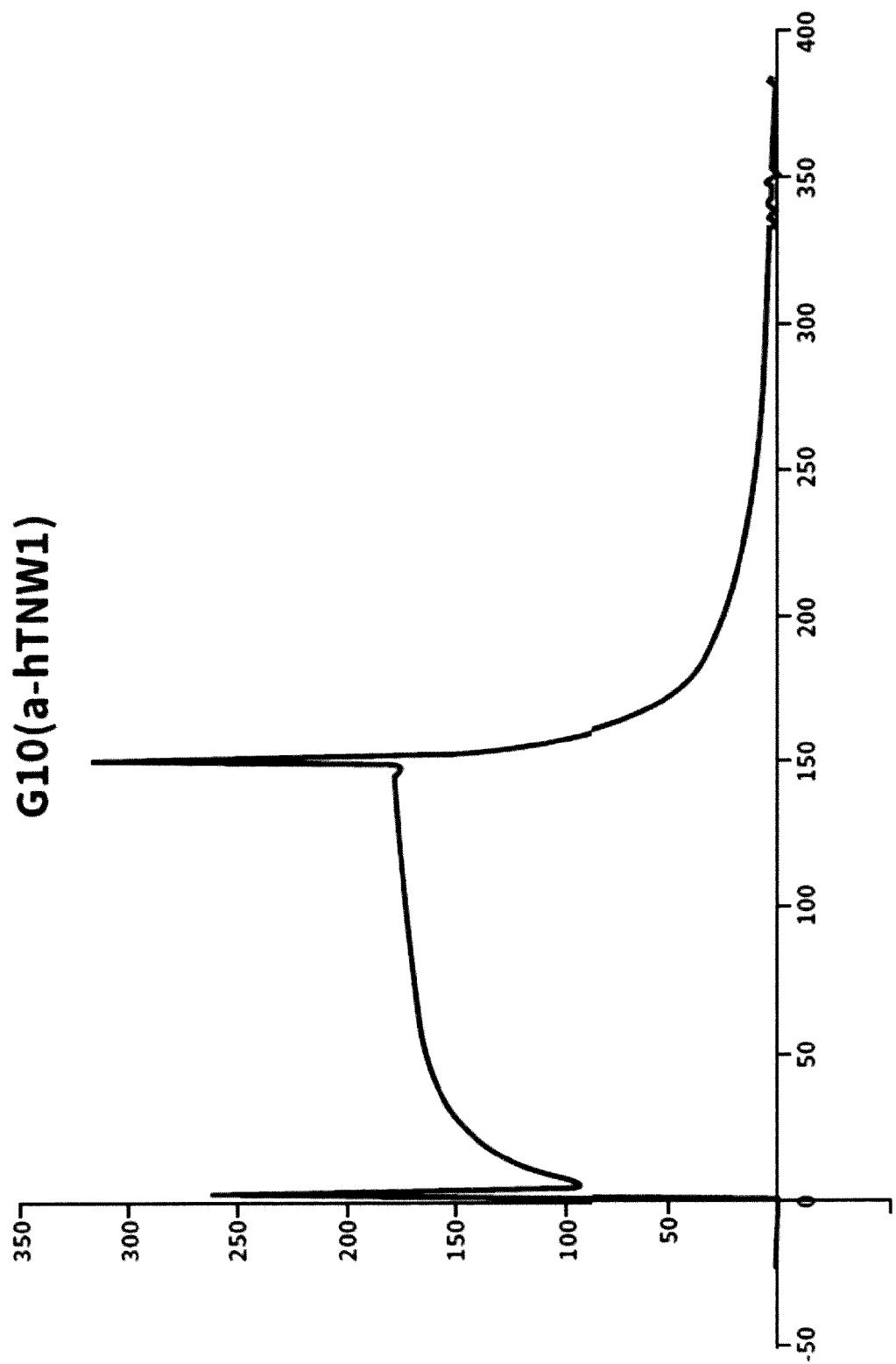
FIG. 7 shows Biacore data demonstrating binding of antibody G10 (in scFv format) to tenascin-W.

The binding of G10 to Tenascin-W was confirmed by Biacore analysis. The results are shown in FIG. 7.

Biacore Analysis:

A monomeric fraction of the purified G10 antibody was analyzed by surface plasmon resonance (BIAcore, 3000 system). A recombinant peptide consisting of amino acids 262-534 of tenascin-W was covalently coupled to the surface of the CM-5 sensor Chip. Twenty-five microliters of each sample were injected at the flow rate of 10 μL/min. The regeneration of the chip was performed with 5 μL of 10 mM glycine-HCl, pH 2.5 (GE Healthcare).

Sequence listing

Amino acid sequences of antibody SW01 specific for the IIICS isoform of fibronectin
SEQ ID NO: 1 (SW01-VH)
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKNR
YIFDYWGQGTLVTVSS SEQ ID NO: 2 (SW01-VL)
SELTQDPAVSVALGQTVRITCQGDSLRSYYASWYQQKPGQAPVLVIYGKN
NRPSGIPDRFSGSSSGNTASLTITGAQAEDEADYYCNSSPKAPRPVVFGG
GTKLTVLG

SEQ ID NO: 3 (SW01-VH CDR1)
GFTFSSYAMS

SEQ ID NO: 4 (SW01-VH CDR2)
AISGSGGSTYYADSVKG

SEQ ID NO: 5 (SW01-VH CDR3)
NRYIFDY

SEQ ID NO: 6 (SW01-VL CDR1)
QGDSLRSYYA

SEQ ID NO: 7 (SW01-VL CDR2)
GKNNRPS

SEQ ID NO: 8 (SW01-VL CDR3)
NSSPKAPRPVV

Amino acid sequences of antibody SW02 specific for the IIICS isoform of fibronectin
SEQ ID NO: 9 (SW02-VH)
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKGR
FLFDYWGQGTLVTVSS SEQ ID NO: 10 (SW02-VL)
SELTQDPAVSVALGQTVRITCQGDSLRSYYASWYQQKPGQAPVLVIYGKN
NRPSGIPDRFSGSSSGNTASLTITGAQAEDEADYYCNSSPLYNPYVVFGG
GTKLTVLG

SEQ ID NO: 11 (SW02-VH CDR1)
GFTFSSYAMS

SEQ ID NO: 12 (SW02-VH CDR2)
AISGSGGSTYYADSVKG

SEQ ID NO: 13 (SW02-VH CDR3)
GRFLFDY

SEQ ID NO: 14 (SW02-VL CDR1)
QGDSLRSYYAS

SEQ ID NO: 15 (SW02-VL CDR2)
GKNNRPS

SEQ ID NO: 16 (SW02-VL CDR3)
NSSPLYNPYVV

Amino acid sequences of antibody CH01 specific for MMP3
SEQ ID NO: 17 (CH01-VH)
EVQLLESGGGLVQPGGSLRLSCAASGFTFSPYAMSWVRQAPGKGLEWVSA
ITGQGGVTYYADSVKGRFTISRDNSKNTLYLQMNSLRAEDTAVYYCAKIS
SFHFDYWGQGTLVTVSS SEQ ID NO: 18 (CH01-VL)
EIVLTQSPGTLSLSPGERATLSCRASQSVSSHHLAWYQQKPGQAPRLLI
YDASSRATGIPDRFSGSGSGTDFTLTISRLEPEDFAVYYCQQPRGAPTTF
GQGTKVEIK

SEQ ID NO: 19 (CH01-VH CDR1)
GFTFSPYAMS

SEQ ID NO: 20 (CH01-VH CDR2)
AITGQGGVTYYADSVKG

| Sequence listing |
|---|
| SEQ ID NO: 21 (CH01-VH CDR3)<br>ISSFHFDY |
| SEQ ID NO: 22 (CH01-VL CDR1)<br>RASQSVSSHHLA |
| SEQ ID NO: 23 (CH01-VL CDR2)<br>DASSRAT |
| SEQ ID NO: 24 (CH01-VL CDR3)<br>QQPRGAPTT |
| Amino acid sequences of antibody LG1 specific for periostin<br>SEQ ID NO: 25 (LG1-VH)<br>EVQLLESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKHT<br>PSFDYWGQGTLVTVSS |
| SEQ ID NO: 26 (LG1-VL)<br>SELTQDPAVSVALGQTVRITCQGDSLRSYYASWYQQKPGQAPVLVIYGK<br>NNRPSGIPDRFSGSSSGNTASLTITGAQAEDEADYYCNSPYRPKKLVVFG<br>GGTKLTVLG |
| SEQ ID NO: 27 (LG1-VH CDR1)<br>GFTFSSYAMS |
| SEQ ID NO: 28 (LG1-VH CDR2)<br>AISGSGGSTYYADSVKG |
| SEQ ID NO: 29 (LG1-VH CDR3)<br>HTPSFDY |
| SEQ ID NO: 30 (LG1-VL CDR1)<br>QGDSLRSYYAS |
| SEQ ID NO: 31 (LG1-VL CDR2)<br>GKNNRPS |
| SEQ ID NO: 32 (LG1-VL CDR3)<br>NSPYRPKKLVV |
| Amino acid sequences of antibody LG2 specific for periostin<br>SEQ ID NO: 33 (LG2-VH)<br>EVQLLESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKAR<br>YPFDYWGQGTLVTVSS |
| SEQ ID NO: 34 (LG2-VL)<br>SELTQDPAVSVALGQTVRITCQGDSLRSYYASWYQQKPGQAPVLVIYGKN<br>NRPSGIPDRFSGSSSGNTASLTITGAQAEDEADYYCNSFGRALPSVVFGG<br>GTKLTVLG |
| SEQ ID NO: 35 (LG2-VH CDR1)<br>GFTFSSYAMS |
| SEQ ID NO: 36 (LG2-VH CDR2)<br>AISGSGGSTYYADSVKG |
| SEQ ID NO: 37 (LG2-VH CDR3)<br>ARYPFDY |
| SEQ ID NO: 38 (LG2-VL CDR1)<br>QGDSLRSYYAS |
| SEQ ID NO: 39 (LG2-VL CDR2)<br>GKNNRPS |
| SEQ ID NO: 40 (LG2-VL CDR3)<br>NSFGRALPSVV |
| Amino acid sequences of antibody LG3 specific for periostin<br>SEQ ID NO: 41 (LG3-VH)<br>EVQLLESGGGLVQPGGSLRLSCAASGFTFSSYAMSWVRQAPGKGLEWVS<br>AISGSGGSTYYADSVKGRFTISRDNSKNTLYLQMNSLRAEDTAVYYCAKR<br>ARLFDYWGQGTLVTVSS |
| SEQ ID NO: 42 (LG3-VL)<br>EIVLTQSPGTLSLSPGERATLSCRASQSVSSSYLAWYQQKPGQAPRLLIY<br>GASSRATGIPDRFSGSGSGTDFTLTISRLEPEDFAVYYCQQGGSLPLTFG<br>QGTKVEIK |
| SEQ ID NO: 43 (LG3-VH CDR1)<br>GFTFSSYAMS |
| SEQ ID NO: 44 (LG3-VH CDR2)<br>AISGSGGSTYYADSVKG |
| SEQ ID NO: 45 (LG3-VH CDR3)<br>RARLFDY |
| SEQ ID NO: 46 (LG3-VL CDR1)<br>RASQSVSSSYLA |
| SEQ ID NO: 47 (LG3-VL CDR2)<br>GASSRAT |
| SEQ ID NO: 48 (LG3-VL CDR3)<br>QQGGSLPLT |
| Amino acid sequences of antibody 1E1 specific for periostin<br>SEQ ID NO: 49 (1E1-VH)<br>EVQLLESGGGLVQPGGSLRLSCAASGFTFSSYAMSWVRQAPGKGLEWVSA<br>ISGSGGSTYYADSVKGRFTISRDNSKNTLYLQMNSLRAEDTAVYYCAKHE<br>PYIGFDYVVGQGTLVTVSS |
| SEQ ID NO: 50 (1E1-VL)<br>SELTQDPAVSVALGQTVRITCQGDSLRTFYASWYQQKPGQAPVLVIYGKN<br>NRPSGIPDRFSGSSSGNTASLTITGAQAEDEADYYCNSSLYPRTPVVFGG<br>GTKLTVLG |
| SEQ ID NO: 51 (1E1-VH CDR1)<br>GFTFSSYAMS |
| SEQ ID NO: 52 (1E1-VH CDR2)<br>AISGSGGSTYYADSVKG |
| SEQ ID NO: 53 (1E1-VH CDR3)<br>HEPYIGFDY |
| SEQ ID NO: 54 (1E1-VL CDR1)<br>QGDSLRTFYAS |
| SEQ ID NO: 55 (1E1-VL CDR2)<br>GKNNRPS |
| SEQ ID NO: 56 (1E1-VL CDR3)<br>NSSLYPRTPVV |
| Amino acid sequences of antibody G10 specific for tenascin W<br>SEQ ID NO: 57 (G10-VH)<br>EVQLLESGGGLVQPGGSLRLSCAASGFTFSSYAMSWVRQAPGKGLEWVSA<br>ISGSGGSTYYADSVKGQFTISRDNSKNTLYLQMNSLRAEDTAVYYCAKAN<br>PWAFDYWGQGTLVTVSS |
| SEQ ID NO: 58 (G10-VL)<br>SELTQDPAVSVALGQTVRITCQGDSLRSYYASWYQQKPGQAPVLVIYGKN<br>NRPSGIPDRFSGSSSGNTASLTITGAQAEDEADYYCNSSGSQRSPVVFGG<br>GTKLTVLG |
| SEQ ID NO: 59 (G10-VH CDR1)<br>GFTFSSYAMS |

Sequence listing

SEQ ID NO: 60 (G10-VH CDR2)
AISGSGGSTYYADSVKG

SEQ ID NO: 61 (G10-VH CDR3)
ANPWAFDY

SEQ ID NO: 62 (G10-VL CDR1)
QGDSLRSYYAS

SEQ ID NO: 63 (G10-VL CDR2)
GKNNRPS

SEQ ID NO: 64 (G10-VL CDR3)
NSSGSQRSPVV

Amino acid sequence of the recombinant tenascin-W peptide used to isolate the G10 antibody
SEQ ID NO: 65
MVVTPQGLQLLKNTEDSLLVSWEPSSQVNHYLLSYYPLGKELSGKQIQVP
KEQHSYEILGLLPGTKYIVTLRNVKNEVSSSPQHLLATTDLAVLGTAWVT
DETENSLDVEWENPSTEVDYYKLRYGPMTGQEVAEVTVPKSSDPKSRYDI
TGLHPGTEYKITVVPMRGELEGKPILLNGRTEIDSPINVVTDRVTEDTAT
VSWDPVQAVIDKYVVRYTSADGDTKEMAVHKDESSTVLTGLKPGEAYKVY
VWAERGNQGSKKADTNALTEIDSPHHHHHH

The invention claimed is:

1. An antibody molecule that binds tenascin W, wherein the antibody molecule comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
    HCDR3 has the amino acid sequence of SEQ ID NO: 61,
    LCDR3 has the amino acid sequence of SEQ ID NO: 64,
    HCDR1 has the amino acid sequence of SEQ ID NO: 59,
    HCDR2 has the amino acid sequence of SEQ ID NO: 60,
    LCDR1 has the amino acid sequence of SEQ ID NO: 62, and
    LCDR2 has the amino acid sequence of SEQ ID NO: 63.

2. The antibody molecule according to claim 1, wherein the VH domain has the amino acid sequence of SEQ ID NO: 57, and/or the VL domain has the amino acid sequence of SEQ ID NO: 58.

3. The antibody molecule according to claim 1, wherein the antibody molecule is or comprises a single chain Fv (scFv), is a small immunoprotein (SIP), is a diabody, or is an IgG molecule.

4. A conjugate comprising an antibody molecule according to claim 1 and a biocidal molecule, a cytotoxic molecule, an anti-inflammatory agent, a radioisotope or a detectable label.

5. A method of treating a tenascin W associated cancer comprising administering an antibody molecule according to claim 1 to a patient in need thereof.

6. An antibody molecule that binds the IIICS isoform of fibronectin, wherein the antibody molecule comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
    HCDR3 has the amino acid sequence of SEQ ID NO: 5,
    LCDR3 has the amino acid sequence of SEQ ID NO: 8,
    HCDR1 has the amino acid sequence of SEQ ID NO: 3,
    HCDR2 has the amino acid sequence of SEQ ID NO: 4,
    LCDR1 has the amino acid sequence of SEQ ID NO: 6, and
    LCDR2 has the amino acid sequence of SEQ ID NO: 7.

7. The antibody molecule according to claim 6, wherein the VH domain has the amino acid sequence of SEQ ID NO: 1, and/or the VL domain has the amino acid sequence of SEQ ID NO: 2.

8. The antibody molecule according to claim 6, wherein the antibody molecule is or comprises a single chain Fv (scFv), is a small immunoprotein (SIP), is a diabody, or is an IgG molecule.

9. A conjugate comprising an antibody molecule according to claim 6 and a biocidal molecule, a cytotoxic molecule, an anti-inflammatory agent, a radioisotope or a detectable label.

10. A method of treating a fibronectin IIICS isoform assocaiated cancer comprising administering an antibody molecule or conjugate according to claim 6 to a patient in need thereof.

11. An antibody molecule that binds matrix-metalloproteinase 3 (MMP3), wherein the antibody molecule comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
  HCDR3 has the amino acid sequence of SEQ ID NO: 21,
  LCDR3 has the amino acid sequence of SEQ ID NO: 24,
  HCDR1 has the amino acid sequence of SEQ ID NO: 19,
  HCDR2 has the amino acid sequence of SEQ ID NO: 20,
  LCDR1 has the amino acid sequence of SEQ ID NO: 22, and
  LCDR2 has the amino acid sequence of SEQ ID NO: 23.

12. The antibody molecule according to claim 11, wherein the VH domain has the amino acid sequence of SEQ ID NO: 17, and/or the VL domain has the amino acid sequence of SEQ ID NO: 18.

13. The antibody molecule according to claim 11, wherein the antibody molecule is or comprises a single chain Fv (scFv), is a small immunoprotein (SIP), is a diabody, or is an IgG molecule.

14. A conjugate comprising an antibody molecule according to claim 11 and a biocidal molecule, a cytotoxic molecule, an anti-inflammatory agent, a radioisotope or a detectable label.

15. A method of treating a matrix-metalloproteinase 3 (MMP3) associated cancer comprising administering an antibody molecule or conjugate according to claim 11 to a patient in need thereof.

16. An antibody molecule that binds periostin, wherein the antibody molecule comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
  HCDR3 has the amino acid sequence of SEQ ID NO: 53,
  LCDR3 has the amino acid sequence of SEQ ID NO: 56,
  HCDR1 has the amino acid sequence of SEQ ID NO: 51,
  HCDR2 has the amino acid sequence of SEQ ID NO: 52,
  LCDR1 has the amino acid sequence of SEQ ID NO: 54, and
  LCDR2 has the amino acid sequence of SEQ ID NO: 55.

17. The antibody molecule according to claim 16, wherein the VH domain has the amino acid sequence of SEQ ID NO: 49, and/or the VL domain has the amino acid sequence of SEQ ID NO: 50.

18. The antibody molecule according to claim 16, wherein the antibody molecule is or comprises a single chain Fv (scFv), is a small immunoprotein (SIP), is a diabody, or is an IgG molecule.

19. A conjugate comprising an antibody molecule according to claim 16 and a biocidal molecule, a cytotoxic molecule, an anti-inflammatory agent, a radioisotope or a detectable label.

20. A method of treating a periostin associated cancer comprising administering an antibody molecule or conjugate according to claim 16 to a patient in need thereof.

* * * * *

SEQUENCE LISTING

<160> NUMBER OF SEQ ID NOS: 65

<210> SEQ ID NO 1
<211> LENGTH: 116
<212> TYPE: PRT
<213> ORGANISM: Artificial sequence
<220> FEATURE:
<223> OTHER INFORMATION: Synthetic amino acid sequence of antibody
      SW01 - VH

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Tyr Ile Phe Asp Tyr Trp Gly Gln Gly Thr Leu Val
            100                 105                 110

Thr Val Ser Ser
            115

<210> SEQ ID NO 2
<211> LENGTH: 108
<212> TYPE: PRT
<213> ORGANISM: Artificial sequence
<220> FEATURE:
<223> OTHER INFORMATION: Synthetic amino acid sequence of antibody
      SW01 - VL

<400> SEQUENCE: 2

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

```
Ser Gly Asn Thr Ala Ser Leu Thr Ile Thr Gly Ala Gln Ala Glu Asp
65                  70                  75                  80

Glu Ala Asp Tyr Tyr Cys Asn Ser Ser Pro Lys Ala Pro Arg Pro Val
                85                  90                  95

Val Phe Gly Gly Gly Thr Lys Leu Thr Val Leu Gly
            100                 105

<210> SEQ ID NO 3
<211> LENGTH: 10
<212> TYPE: PRT
<213> ORGANISM: Artificial sequence
<220> FEATURE:
<223> OTHER INFORMATION: Synthetic amino acid sequence of antibody
      SW01 - VH CDR1

<400> SEQUENCE: 3

Gly Phe Thr Phe Ser Ser Tyr Ala Met Ser
1               5                   10

<210> SEQ ID NO 4
<211> LENGTH: 17
<212> TYPE: PRT
<213> ORGANISM: Artificial sequence
<220> FEATURE:
<223> OTHER INFORMATION: Synthetic amino acid sequence of antibody
      SW01 - VH CDR2

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 7
<212> TYPE: PRT
<213> ORGANISM: Artificial sequence
<220> FEATURE:
<223> OTHER INFORMATION: Synthetic amino acid sequence of antibody
      SW01 - VH CDR3

<400> SEQUENCE: 5

Asn Arg Tyr Ile Phe Asp Tyr
1               5

<210> SEQ ID NO 6
<211> LENGTH: 11
<212> TYPE: PRT
<213> ORGANISM: Artificial sequence
<220> FEATURE:
<223> OTHER INFORMATION: Synthetic amino acid sequence of antibody
      SW01 - VL CDR1

<400> SEQUENCE: 6

Gln Gly Asp Ser Leu Arg Ser Tyr Tyr Ala Ser
1               5                   10

<210> SEQ ID NO 7
<211> LENGTH: 7
<212> TYPE: PRT
<213> ORGANISM: Artificial sequence
<220> FEATURE:
<223> OTHER INFORMATION: Synthetic amino acid sequence of antibody
      SW01 - VL CDR2

<400> SEQUENCE: 7
```

Gly Lys Asn Asn Arg Pro Ser
1               5

<210> SEQ ID NO 8
<211> LENGTH: 11
<212> TYPE: PRT
<213> ORGANISM: Artificial sequence
<220> FEATURE:
<223> OTHER INFORMATION: Synthetic amino acid sequence of antibody
      SW01 - VL CDR3

<400> SEQUENCE: 8

Asn Ser Ser Pro Lys Ala Pro Arg Pro Val Val
1               5                   10

<210> SEQ ID NO 9
<211> LENGTH: 116
<212> TYPE: PRT
<213> ORGANISM: Artificial sequence
<220> FEATURE:
<223> OTHER INFORMATION: Synthetic amino acid sequence of antibody
      SW02 - VH

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Phe Leu Phe Asp Tyr Trp Gly Gln Gly Thr Leu Val
            100                 105                 110

Thr Val Ser Ser
        115

<210> SEQ ID NO 10
<211> LENGTH: 108
<212> TYPE: PRT
<213> ORGANISM: Artificial sequence
<220> FEATURE:
<223> OTHER INFORMATION: Synthetic amino acid sequence of antibody
      SW02 - VL

<400> SEQUENCE: 10

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ser Pro Leu Tyr Asn Pro Tyr Val

Val Phe Gly Gly Gly Thr Lys Leu Thr Val Leu Gly
            100                 105

<210> SEQ ID NO 11
<211> LENGTH: 10
<212> TYPE: PRT
<213> ORGANISM: Artificial sequence
<220> FEATURE:
<223> OTHER INFORMATION: Synthetic amino acid sequence of antibody
      SW02 - VH CDR1

<400> SEQUENCE: 11

Gly Phe Thr Phe Ser Ser Tyr Ala Met Ser
1               5                   10

<210> SEQ ID NO 12
<211> LENGTH: 17
<212> TYPE: PRT
<213> ORGANISM: Artificial sequence
<220> FEATURE:
<223> OTHER INFORMATION: Synthetic amino acid sequence of antibody
      SW02 - VH CDR2

<400> SEQUENCE: 12

Ala Ile Ser Gly Ser Gly Gly Ser Thr Tyr Tyr Ala Asp Ser Val Lys
1               5                   10                  15
Gly

<210> SEQ ID NO 13
<211> LENGTH: 7
<212> TYPE: PRT
<213> ORGANISM: Artificial sequence
<220> FEATURE:
<223> OTHER INFORMATION: Synthetic amino acid sequence of antibody
      SW02 - VH CDR3

<400> SEQUENCE: 13

Gly Arg Phe Leu Phe Asp Tyr
1               5

<210> SEQ ID NO 14
<211> LENGTH: 11
<212> TYPE: PRT
<213> ORGANISM: Artificial sequence
<220> FEATURE:
<223> OTHER INFORMATION: Synthetic amino acid sequence of antibody
      SW02 - VL CDR1

<400> SEQUENCE: 14

Gln Gly Asp Ser Leu Arg Ser Tyr Tyr Ala Ser
1               5                   10

<210> SEQ ID NO 15
<211> LENGTH: 7
<212> TYPE: PRT
<213> ORGANISM: Artificial sequence
<220> FEATURE:
<223> OTHER INFORMATION: Synthetic amino acid sequence of antibody
      SW02 - VL CDR2

<400> SEQUENCE: 15

Gly Lys Asn Asn Arg Pro Ser
1               5

<210> SEQ ID NO 16

```
<211> LENGTH: 11
<212> TYPE: PRT
<213> ORGANISM: Artificial sequence
<220> FEATURE:
<223> OTHER INFORMATION: Synthetic amino acid sequence of antibody
      SW02 - VL CDR3

<400> SEQUENCE: 16

Asn Ser Ser Pro Leu Tyr Asn Pro Tyr Val Val
1               5                   10

<210> SEQ ID NO 17
<211> LENGTH: 117
<212> TYPE: PRT
<213> ORGANISM: Artificial sequence
<220> FEATURE:
<223> OTHER INFORMATION: Synthetic amino acid sequence of antibody
      CH01 - VH

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Ala Met Ser Trp Val Arg Gln Ala Pro Gly Lys Gly Leu Glu Trp Val
        35                  40                  45

Ser Ala Ile Thr Gly Gln Gly Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Ser Phe His Phe Asp Tyr Trp Gly Gln Gly Thr Leu
            100                 105                 110

Val Thr Val Ser Ser
        115

<210> SEQ ID NO 18
<211> LENGTH: 108
<212> TYPE: PRT
<213> ORGANISM: Artificial sequence
<220> FEATURE:
<223> OTHER INFORMATION: Synthetic amino acid sequence of antibody
      CH01 - VL

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser His
            20                  25                  30

His Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Pro Arg Gly Ala Pro
                85                  90                  95

Thr Thr Phe Gly Gln Gly Thr Lys Val Glu Ile Lys
            100                 105
```

```
<210> SEQ ID NO 19
<211> LENGTH: 10
<212> TYPE: PRT
<213> ORGANISM: Artificial sequence
<220> FEATURE:
<223> OTHER INFORMATION: Synthetic amino acid sequence of antibody
      CH01 - VH CDR1

<400> SEQUENCE: 19

Gly Phe Thr Phe Ser Pro Tyr Ala Met Ser
1               5                   10

<210> SEQ ID NO 20
<211> LENGTH: 17
<212> TYPE: PRT
<213> ORGANISM: Artificial sequence
<220> FEATURE:
<223> OTHER INFORMATION: Synthetic amino acid sequence of antibody
      CH01 - VH CDR2

<400> SEQUENCE: 20

Ala Ile Thr Gly Gln Gly Gly Val Thr Tyr Tyr Ala Asp Ser Val Lys
1               5                   10                  15

Gly

<210> SEQ ID NO 21
<211> LENGTH: 8
<212> TYPE: PRT
<213> ORGANISM: Artificial sequence
<220> FEATURE:
<223> OTHER INFORMATION: Synthetic amino acid sequence of antibody
      CH01 - VH CDR3

<400> SEQUENCE: 21

Ile Ser Ser Phe His Phe Asp Tyr
1               5

<210> SEQ ID NO 22
<211> LENGTH: 12
<212> TYPE: PRT
<213> ORGANISM: Artificial sequence
<220> FEATURE:
<223> OTHER INFORMATION: Synthetic amino acid sequence of antibody
      CH01 - VL CDR1

<400> SEQUENCE: 22

Arg Ala Ser Gln Ser Val Ser Ser His His Leu Ala
1               5                   10

<210> SEQ ID NO 23
<211> LENGTH: 7
<212> TYPE: PRT
<213> ORGANISM: Artificial sequence
<220> FEATURE:
<223> OTHER INFORMATION: Synthetic amino acid sequence of antibody
      CH01 - VL CDR2

<400> SEQUENCE: 23

Asp Ala Ser Ser Arg Ala Thr
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic amino acid sequence of antibody
```

CH01 - VL CDR3

<400> SEQUENCE: 24

Gln Gln Pro Arg Gly Ala Pro Thr Thr
1               5

<210> SEQ ID NO 25
<211> LENGTH: 116
<212> TYPE: PRT
<213> ORGANISM: Artificial sequence
<220> FEATURE:
<223> OTHER INFORMATION: Synthetic amino acid sequence of antibody
      LG1 - VH

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Thr Pro Ser Phe Asp Tyr Trp Gly Gln Gly Thr Leu Val
            100                 105                 110

Thr Val Ser Ser
        115

<210> SEQ ID NO 26
<211> LENGTH: 108
<212> TYPE: PRT
<213> ORGANISM: Artificial sequence
<220> FEATURE:
<223> OTHER INFORMATION: Synthetic amino acid sequence of antibody
      LG1 - VL

<400> SEQUENCE: 26

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Pro Tyr Arg Pro Lys Lys Leu Val
                85                  90                  95

Val Phe Gly Gly Gly Thr Lys Leu Thr Val Leu Gly
            100                 105

<210> SEQ ID NO 27
<211> LENGTH: 10
<212> TYPE: PRT
<213> ORGANISM: Artificial sequence

```
<220> FEATURE:
<223> OTHER INFORMATION: Synthetic amino acid sequence of antibody
      LG1 - VH CDR1

<400> SEQUENCE: 27

Gly Phe Thr Phe Ser Ser Tyr Ala Met Ser
1               5                   10

<210> SEQ ID NO 28
<211> LENGTH: 17
<212> TYPE: PRT
<213> ORGANISM: Artificial sequence
<220> FEATURE:
<223> OTHER INFORMATION: Synthetic amino acid sequence of antibody
      LG1 - VH CDR2

<400> SEQUENCE: 28

Ala Ile Ser Gly Ser Gly Gly Ser Thr Tyr Tyr Ala Asp Ser Val Lys
1               5                   10                  15

Gly

<210> SEQ ID NO 29
<211> LENGTH: 7
<212> TYPE: PRT
<213> ORGANISM: Artificial sequence
<220> FEATURE:
<223> OTHER INFORMATION: Synthetic amino acid sequence of antibody
      LG1 - VH CDR3

<400> SEQUENCE: 29

His Thr Pro Ser Phe Asp Tyr
1               5

<210> SEQ ID NO 30
<211> LENGTH: 11
<212> TYPE: PRT
<213> ORGANISM: Artificial sequence
<220> FEATURE:
<223> OTHER INFORMATION: Synthetic amino acid sequence of antibody
      LG1 - VL CDR1

<400> SEQUENCE: 30

Gln Gly Asp Ser Leu Arg Ser Tyr Tyr Ala Ser
1               5                   10

<210> SEQ ID NO 31
<211> LENGTH: 7
<212> TYPE: PRT
<213> ORGANISM: Artificial sequence
<220> FEATURE:
<223> OTHER INFORMATION: Synthetic amino acid sequence of antibody
      LG1 - VL CDR2

<400> SEQUENCE: 31

Gly Lys Asn Asn Arg Pro Ser
1               5

<210> SEQ ID NO 32
<211> LENGTH: 11
<212> TYPE: PRT
<213> ORGANISM: Artificial sequence
<220> FEATURE:
<223> OTHER INFORMATION: Synthetic amino acid sequence of antibody
      LG1 - VL CDR3

<400> SEQUENCE: 32

Asn Ser Pro Tyr Arg Pro Lys Lys Leu Val Val
```

<210> SEQ ID NO 33
<211> LENGTH: 116
<212> TYPE: PRT
<213> ORGANISM: Artificial sequence
<220> FEATURE:
<223> OTHER INFORMATION: Synthetic amino acid sequence of antibody
    LG2 - VH

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Arg Tyr Pro Phe Asp Tyr Trp Gly Gln Gly Thr Leu Val
            100                 105                 110

Thr Val Ser Ser
        115
```

<210> SEQ ID NO 34
<211> LENGTH: 108
<212> TYPE: PRT
<213> ORGANISM: Artificial sequence
<220> FEATURE:
<223> OTHER INFORMATION: Synthetic amino acid sequence of antibody
    LG2 - VL

<400> SEQUENCE: 34

```
Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Phe Gly Arg Ala Leu Pro Ser Val
                85                  90                  95

Val Phe Gly Gly Gly Thr Lys Leu Thr Val Leu Gly
            100                 105
```

<210> SEQ ID NO 35
<211> LENGTH: 10
<212> TYPE: PRT
<213> ORGANISM: Artificial sequence
<220> FEATURE:
<223> OTHER INFORMATION: Synthetic amino acid sequence of antibody
    LG2 - VH CDR1

<400> SEQUENCE: 35

Gly Phe Thr Phe Ser Ser Tyr Ala Met Ser
1               5                   10

<210> SEQ ID NO 36
<211> LENGTH: 17
<212> TYPE: PRT
<213> ORGANISM: Artificial sequence
<220> FEATURE:
<223> OTHER INFORMATION: Synthetic amino acid sequence of antibody
      LG2 - VH CDR2

<400> SEQUENCE: 36

Ala Ile Ser Gly Ser Gly Gly Ser Thr Tyr Tyr Ala Asp Ser Val Lys
1               5                   10                  15
Gly

<210> SEQ ID NO 37
<211> LENGTH: 7
<212> TYPE: PRT
<213> ORGANISM: Artificial sequence
<220> FEATURE:
<223> OTHER INFORMATION: Synthetic amino acid sequence of antibody
      LG2 - VH CDR3

<400> SEQUENCE: 37

Ala Arg Tyr Pro Phe Asp Tyr
1               5

<210> SEQ ID NO 38
<211> LENGTH: 11
<212> TYPE: PRT
<213> ORGANISM: Artificial sequence
<220> FEATURE:
<223> OTHER INFORMATION: Synthetic amino acid sequence of antibody
      LG2 - VL CDR1

<400> SEQUENCE: 38

Gln Gly Asp Ser Leu Arg Ser Tyr Tyr Ala Ser
1               5                   10

<210> SEQ ID NO 39
<211> LENGTH: 7
<212> TYPE: PRT
<213> ORGANISM: Artificial sequence
<220> FEATURE:
<223> OTHER INFORMATION: Synthetic amino acid sequence of antibody
      LG2 - VL CDR2

<400> SEQUENCE: 39

Gly Lys Asn Asn Arg Pro Ser
1               5

<210> SEQ ID NO 40
<211> LENGTH: 11
<212> TYPE: PRT
<213> ORGANISM: Artificial sequence
<220> FEATURE:
<223> OTHER INFORMATION: Synthetic amino acid sequence of antibody
      LG2 - VL CDR3

<400> SEQUENCE: 40

Asn Ser Phe Gly Arg Ala Leu Pro Ser Val Val
1               5                   10

<210> SEQ ID NO 41
<211> LENGTH: 116

```
<212> TYPE: PRT
<213> ORGANISM: Artificial sequence
<220> FEATURE:
<223> OTHER INFORMATION: Synthetic amino acid sequence of antibody
      LG3 - VH

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ala Arg Leu Phe Asp Tyr Trp Gly Gln Gly Thr Leu Val
            100                 105                 110

Thr Val Ser Ser
        115

<210> SEQ ID NO 42
<211> LENGTH: 108
<212> TYPE: PRT
<213> ORGANISM: Artificial sequence
<220> FEATURE:
<223> OTHER INFORMATION: Synthetic amino acid sequence of antibody
      LG3 - VL

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Leu Pro
                85                  90                  95

Leu Thr Phe Gly Gln Gly Thr Lys Val Glu Ile Lys
            100                 105

<210> SEQ ID NO 43
<211> LENGTH: 10
<212> TYPE: PRT
<213> ORGANISM: Artificial sequence
<220> FEATURE:
<223> OTHER INFORMATION: Synthetic amino acid sequence of antibody
      LG3 - VH CDR1

<400> SEQUENCE: 43

Gly Phe Thr Phe Ser Ser Tyr Ala Met Ser
1               5                   10
```

```
<210> SEQ ID NO 44
<211> LENGTH: 17
<212> TYPE: PRT
<213> ORGANISM: Artificial sequence
<220> FEATURE:
<223> OTHER INFORMATION: Synthetic amino acid sequence of antibody
      LG3 - VH CDR2

<400> SEQUENCE: 44

Ala Ile Ser Gly Ser Gly Gly Ser Thr Tyr Tyr Ala Asp Ser Val Lys
1               5                   10                  15

Gly

<210> SEQ ID NO 45
<211> LENGTH: 7
<212> TYPE: PRT
<213> ORGANISM: Artificial sequence
<220> FEATURE:
<223> OTHER INFORMATION: Synthetic amino acid sequence of antibody
      LG3 - VH CDR3

<400> SEQUENCE: 45

Arg Ala Arg Leu Phe Asp Tyr
1               5

<210> SEQ ID NO 46
<211> LENGTH: 12
<212> TYPE: PRT
<213> ORGANISM: Artificial sequence
<220> FEATURE:
<223> OTHER INFORMATION: Synthetic amino acid sequence of antibody
      LG3 - VL CDR1

<400> SEQUENCE: 46

Arg Ala Ser Gln Ser Val Ser Ser Ser Tyr Leu Ala
1               5                   10

<210> SEQ ID NO 47
<211> LENGTH: 7
<212> TYPE: PRT
<213> ORGANISM: Artificial sequence
<220> FEATURE:
<223> OTHER INFORMATION: Synthetic amino acid sequence of antibody
      LG3 - VL CDR2

<400> SEQUENCE: 47

Gly Ala Ser Ser Arg Ala Thr
1               5

<210> SEQ ID NO 48
<211> LENGTH: 9
<212> TYPE: PRT
<213> ORGANISM: Artificial sequence
<220> FEATURE:
<223> OTHER INFORMATION: Synthetic amino acid sequence of antibody
      LG3 - VL CDR3

<400> SEQUENCE: 48

Gln Gln Gly Gly Ser Leu Pro Leu Thr
1               5

<210> SEQ ID NO 49
<211> LENGTH: 118
<212> TYPE: PRT
<213> ORGANISM: Artificial sequence
<220> FEATURE:
<223> OTHER INFORMATION: Synthetic amino acid sequence of antibody
      1E1- VH
```

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Glu Pro Tyr Ile Gly Phe Asp Tyr Trp Gly Gln Gly Thr
            100                 105                 110

Leu Val Thr Val Ser Ser
            115

<210> SEQ ID NO 50
<211> LENGTH: 108
<212> TYPE: PRT
<213> ORGANISM: Artificial sequence
<220> FEATURE:
<223> OTHER INFORMATION: Synthetic amino acid sequence of antibody
      1E1- VL

<400> SEQUENCE: 50

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Thr Phe Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ser Leu Tyr Pro Arg Thr Pro Val
                85                  90                  95

Val Phe Gly Gly Gly Thr Lys Leu Thr Val Leu Gly
            100                 105

<210> SEQ ID NO 51
<211> LENGTH: 10
<212> TYPE: PRT
<213> ORGANISM: Artificial sequence
<220> FEATURE:
<223> OTHER INFORMATION: Synthetic amino acid sequence of antibody
      1E1- VH CDR1

<400> SEQUENCE: 51

Gly Phe Thr Phe Ser Ser Tyr Ala Met Ser
1               5                   10

<210> SEQ ID NO 52
<211> LENGTH: 17
<212> TYPE: PRT
<213> ORGANISM: Artificial sequence
<220> FEATURE:

<223> OTHER INFORMATION: Synthetic amino acid sequence of antibody
      1E1- VH CDR2

<400> SEQUENCE: 52

Ala Ile Ser Gly Ser Gly Gly Ser Thr Tyr Tyr Ala Asp Ser Val Lys
1               5                   10                  15

Gly

<210> SEQ ID NO 53
<211> LENGTH: 9
<212> TYPE: PRT
<213> ORGANISM: Artificial sequence
<220> FEATURE:
<223> OTHER INFORMATION: Synthetic amino acid sequence of antibody
      1E1- VH CDR3

<400> SEQUENCE: 53

His Glu Pro Tyr Ile Gly Phe Asp Tyr
1               5

<210> SEQ ID NO 54
<211> LENGTH: 11
<212> TYPE: PRT
<213> ORGANISM: Artificial sequence
<220> FEATURE:
<223> OTHER INFORMATION: Synthetic amino acid sequence of antibody
      1E1- VL CDR1

<400> SEQUENCE: 54

Gln Gly Asp Ser Leu Arg Thr Phe Tyr Ala Ser
1               5                   10

<210> SEQ ID NO 55
<211> LENGTH: 7
<212> TYPE: PRT
<213> ORGANISM: Artificial sequence
<220> FEATURE:
<223> OTHER INFORMATION: Synthetic amino acid sequence of antibody
      1E1- VL CDR2

<400> SEQUENCE: 55

Gly Lys Asn Asn Arg Pro Ser
1               5

<210> SEQ ID NO 56
<211> LENGTH: 11
<212> TYPE: PRT
<213> ORGANISM: Artificial sequence
<220> FEATURE:
<223> OTHER INFORMATION: Synthetic amino acid sequence of antibody
      1E1- VL CDR3

<400> SEQUENCE: 56

Asn Ser Ser Leu Tyr Pro Arg Thr Pro Val Val
1               5                   10

<210> SEQ ID NO 57
<211> LENGTH: 117
<212> TYPE: PRT
<213> ORGANISM: Artificial sequence
<220> FEATURE:
<223> OTHER INFORMATION: Synthetic amino acid sequence of antibody
      G10 - VH

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Gln Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ala Asn Pro Trp Ala Phe Asp Tyr Trp Gly Gln Gly Thr Leu
                100                 105                 110

Val Thr Val Ser Ser
            115

<210> SEQ ID NO 58
<211> LENGTH: 108
<212> TYPE: PRT
<213> ORGANISM: Artificial sequence
<220> FEATURE:
<223> OTHER INFORMATION: Synthetic amino acid sequence of antibody
      G10 - VL

<400> SEQUENCE: 58

Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
            35                  40                  45

Lys Asn Asn Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Ser Gly Ser Gln Arg Ser Pro Val
                85                  90                  95

Val Phe Gly Gly Gly Thr Lys Leu Thr Val Leu Gly
                100                 105

<210> SEQ ID NO 59
<211> LENGTH: 10
<212> TYPE: PRT
<213> ORGANISM: Artificial sequence
<220> FEATURE:
<223> OTHER INFORMATION: Synthetic amino acid sequence of antibody
      G10 - VH CDR1

<400> SEQUENCE: 59

Gly Phe Thr Phe Ser Ser Tyr Ala Met Ser
 1               5                  10

<210> SEQ ID NO 60
<211> LENGTH: 17
<212> TYPE: PRT
<213> ORGANISM: Artificial sequence
<220> FEATURE:
<223> OTHER INFORMATION: Synthetic amino acid sequence of antibody
      G10 - VH CDR2

<400> SEQUENCE: 60

```
Ala Ile Ser Gly Ser Gly Gly Ser Thr Tyr Tyr Ala Asp Ser Val Lys
1               5                   10                  15

Gly

<210> SEQ ID NO 61
<211> LENGTH: 8
<212> TYPE: PRT
<213> ORGANISM: Artificial sequence
<220> FEATURE:
<223> OTHER INFORMATION: Synthetic amino acid sequence of antibody
      G10 - VH CDR3

<400> SEQUENCE: 61

Ala Asn Pro Trp Ala Phe Asp Tyr
1               5

<210> SEQ ID NO 62
<211> LENGTH: 11
<212> TYPE: PRT
<213> ORGANISM: Artificial sequence
<220> FEATURE:
<223> OTHER INFORMATION: Synthetic amino acid sequence of antibody
      G10 - VL CDR1

<400> SEQUENCE: 62

Gln Gly Asp Ser Leu Arg Ser Tyr Tyr Ala Ser
1               5                   10

<210> SEQ ID NO 63
<211> LENGTH: 7
<212> TYPE: PRT
<213> ORGANISM: Artificial sequence
<220> FEATURE:
<223> OTHER INFORMATION: Synthetic amino acid sequence of antibod
      y G10 - VL CDR2

<400> SEQUENCE: 63

Gly Lys Asn Asn Arg Pro Ser
1               5

<210> SEQ ID NO 64
<211> LENGTH: 11
<212> TYPE: PRT
<213> ORGANISM: Artificial sequence
<220> FEATURE:
<223> OTHER INFORMATION: Synthetic amino acid sequence of antibody
      G10 - VL CDR3

<400> SEQUENCE: 64

Asn Ser Ser Gly Ser Gln Arg Ser Pro Val Val
1               5                   10

<210> SEQ ID NO 65
<211> LENGTH: 280
<212> TYPE: PRT
<213> ORGANISM: Artificial sequence
<220> FEATURE:
<223> OTHER INFORMATION: Synthetic sequence - Amino acid sequence of
      the recombinant tenascin-W peptide used to isolate the G10
      antibody

<400> SEQUENCE: 65

Met Val Val Thr Pro Gln Gly Leu Gln Leu Leu Lys Asn Thr Glu Asp
1               5                   10                  15

Ser Leu Leu Val Ser Trp Glu Pro Ser Ser Gln Val Asn His Tyr Leu
                20                  25                  30
```

-continued

```
Leu Ser Tyr Tyr Pro Leu Gly Lys Glu Leu Ser Gly Lys Gln Ile Gln
        35              40              45

Val Pro Lys Glu Gln His Ser Tyr Glu Ile Leu Gly Leu Leu Pro Gly
50              55                      60

Thr Lys Tyr Ile Val Thr Leu Arg Asn Val Lys Asn Glu Val Ser Ser
65              70              75                      80

Ser Pro Gln His Leu Leu Ala Thr Thr Asp Leu Ala Val Leu Gly Thr
                85              90                      95

Ala Trp Val Thr Asp Glu Thr Glu Asn Ser Leu Asp Val Glu Trp Glu
            100             105             110

Asn Pro Ser Thr Glu Val Asp Tyr Tyr Lys Leu Arg Tyr Gly Pro Met
            115             120             125

Thr Gly Gln Glu Val Ala Glu Val Thr Val Pro Lys Ser Ser Asp Pro
    130             135             140

Lys Ser Arg Tyr Asp Ile Thr Gly Leu His Pro Gly Thr Glu Tyr Lys
145             150             155             160

Ile Thr Val Val Pro Met Arg Gly Glu Leu Glu Gly Lys Pro Ile Leu
                165             170             175

Leu Asn Gly Arg Thr Glu Ile Asp Ser Pro Thr Asn Val Val Thr Asp
            180             185             190

Arg Val Thr Glu Asp Thr Ala Thr Val Ser Trp Asp Pro Val Gln Ala
            195             200             205

Val Ile Asp Lys Tyr Val Val Arg Tyr Thr Ser Ala Asp Gly Asp Thr
            210             215             220

Lys Glu Met Ala Val His Lys Asp Glu Ser Ser Thr Val Leu Thr Gly
225             230             235             240

Leu Lys Pro Gly Glu Ala Tyr Lys Val Tyr Val Trp Ala Glu Arg Gly
                245             250             255

Asn Gln Gly Ser Lys Lys Ala Asp Thr Asn Ala Leu Thr Glu Ile Asp
            260             265             270

Ser Pro His His His His His His
            275             280
```